(12) United States Patent
Carstens

(10) Patent No.: US 7,846,145 B2
(45) Date of Patent: Dec. 7, 2010

(54) BODY CONFORMING TEXTILE HOLDER AND ABSORBENT ARTICLE

(75) Inventor: Jerry Edward Carstens, West Chester, OH (US)

(73) Assignee: RUSL, LLC, West Chester, OH (US)

( * ) Notice: Subject to any disclaimer, the term of this patent is extended or adjusted under 35 U.S.C. 154(b) by 861 days.

(21) Appl. No.: 11/269,255

(22) Filed: Nov. 8, 2005

(65) Prior Publication Data

US 2007/0106242 A1 May 10, 2007

(51) Int. Cl.
*A61F 13/15* (2006.01)
(52) U.S. Cl. ............................ 604/385.22; 604/385.26; 604/385.01; 604/396
(58) Field of Classification Search ............ 604/385.01, 604/385.22, 385.24, 385.26, 402, 400, 396
See application file for complete search history.

(56) References Cited

U.S. PATENT DOCUMENTS

| | | | |
|---|---|---|---|
| 2,573,791 A | 11/1951 | Howells |
| 2,792,698 A | 5/1957 | Hampp |
| 2,837,095 A | 6/1958 | Stevenson |
| 2,946,211 A | 7/1960 | Morancy |
| 3,098,369 A | 7/1963 | Burleson et al. |
| 3,299,890 A | 1/1967 | Parker |
| 3,307,546 A | 3/1967 | Vittoria et al. |
| 3,368,563 A | 2/1968 | Scheier |
| 3,504,672 A | 4/1970 | Moon |
| 3,513,668 A | 5/1970 | Mintz |
| 3,552,154 A | 1/1971 | Lesley |
| 3,578,546 A | 5/1971 | Morancy |
| 3,900,035 A | 8/1975 | Welch et al. |
| 3,910,075 A | 10/1975 | Holliday |
| 3,943,912 A | 3/1976 | Nakayama |
| 3,950,789 A | 4/1976 | Konz et al. |
| 4,005,494 A | 2/1977 | Burn |
| 4,014,047 A | 3/1977 | Zobel |
| 4,038,699 A | 8/1977 | Burn |
| 4,135,653 A | 1/1979 | Sieloff |
| 4,190,054 A | 2/1980 | Brennan |
| 4,195,629 A | 4/1980 | Halford |
| 4,204,543 A | 5/1980 | Henderson |
| 4,207,885 A | 6/1980 | Hampton et al. |
| 4,231,356 A | 11/1980 | Usukura |
| 4,289,137 A | 9/1981 | Dell et al. |

(Continued)

OTHER PUBLICATIONS

Labels on package for product: Therma Care™ Heatwraps (Back/Hip), Procter & Gamble, marketed prior to Nov. 2004.
Labels on package for product: Therma Care™ Heatwraps (Knee), Procter & Gamble, marketed prior to Nov. 2004.
Labels on package for product: Therma Care™ Heatwraps (Menstrual Patches), Procter & Gamble, marketed prior to Nov. 2004.

(Continued)

*Primary Examiner*—Jacqueline F. Stephens
(74) *Attorney, Agent, or Firm*—Hasse & Nesbitt LLC; Donald E. Hasse

(57) ABSTRACT

A body conforming, reusable, washable, textile holder for removably holding at least one article in close bodily contact. The holder may be a wrap or tube constructed to enclose a portion of the body where the article is to be held. The article may be a therapeutic article, such as a heat generating thermal pack, a cooling pack, or other article comprising a therapeutic agent; an absorbent article; a sensing article; or a filter article. The invention also relates to a system comprising the body conforming holder and an article for use therewith, and a method for holding such an article in close bodily contact by wearing the holder.

22 Claims, 10 Drawing Sheets

U.S. PATENT DOCUMENTS

| | | | |
|---|---|---|---|
| 4,300,240 A | 11/1981 | Edwards |
| 4,326,533 A | 4/1982 | Henderson |
| 4,366,804 A | 1/1983 | Abe |
| 4,432,477 A | 2/1984 | Haidt et al. |
| 4,445,233 A | 5/1984 | Rubin |
| 4,470,417 A | 9/1984 | Gruber |
| 4,498,200 A | 2/1985 | Livingstone |
| 4,500,019 A | 2/1985 | Curley |
| 4,509,667 A | 4/1985 | Meldrum |
| 4,520,509 A | 6/1985 | Ward |
| 4,522,190 A | 6/1985 | Kuhn et al. |
| 4,527,403 A | 7/1985 | Fullbright et al. |
| 4,527,566 A | 7/1985 | Abare |
| RE32,026 E | 11/1985 | Yamashita et al. |
| 4,556,055 A | 12/1985 | Bonner, Jr. |
| 4,563,184 A | 1/1986 | Korol |
| 4,573,447 A | 3/1986 | Thrash et al. |
| 4,576,169 A | 3/1986 | Williams |
| 4,586,506 A | 5/1986 | Nangle |
| 4,641,379 A | 2/1987 | Martin |
| 4,649,895 A | 3/1987 | Yasuki et al. |
| 4,671,267 A | 6/1987 | Stout |
| 4,676,247 A | 6/1987 | Van Cleve |
| 4,688,572 A | 8/1987 | Hubbard et al. |
| 4,753,241 A | 6/1988 | Brannigan et al. |
| 4,777,073 A | 10/1988 | Sheth |
| 4,802,473 A | 2/1989 | Hubbard et al. |
| 4,825,474 A | 5/1989 | Edwards |
| 4,860,748 A | 8/1989 | Chiurco et al. |
| 4,886,063 A | 12/1989 | Crews |
| 4,891,501 A | 1/1990 | Lipton |
| 4,935,287 A | 6/1990 | Johnson et al. |
| 4,949,401 A | 8/1990 | Kimsey |
| 4,950,264 A | 8/1990 | Osborn, III |
| 4,961,235 A | 10/1990 | Williger |
| 4,972,832 A | 11/1990 | Trapini et al. |
| 4,974,762 A | 12/1990 | Boretsky et al. |
| 4,981,135 A | 1/1991 | Hardy |
| 4,990,147 A | 2/1991 | Freeland |
| 5,000,176 A | 3/1991 | Daniel |
| 5,005,374 A | 4/1991 | Spitler |
| 5,009,653 A | 4/1991 | Osborn, III |
| 5,020,711 A | 6/1991 | Kelley |
| 5,035,006 A | 7/1991 | Hetz et al. |
| 5,038,779 A | 8/1991 | Barry et al. |
| 5,046,479 A | 9/1991 | Usui |
| 5,062,414 A | 11/1991 | Grim |
| 5,072,598 A | 12/1991 | Dibrell |
| 5,088,549 A | 2/1992 | Schneider |
| 5,107,547 A | 4/1992 | Scheu |
| 5,144,694 A | 9/1992 | Conrad Da oud et al. |
| 5,146,625 A | 9/1992 | Steele et al. |
| 5,148,804 A | 9/1992 | Hill et al. |
| 5,179,942 A | 1/1993 | Drulias et al. |
| 5,188,103 A | 2/1993 | Smith |
| 5,207,663 A | 5/1993 | McQueen |
| 5,214,804 A | 6/1993 | Carey et al. |
| 5,215,080 A | 6/1993 | Thomas et al. |
| 5,221,031 A | 6/1993 | Prigmore |
| 5,230,333 A | 7/1993 | Yates et al. |
| 5,274,850 A | 1/1994 | Aldridge |
| 5,295,949 A | 3/1994 | Hathaway |
| 5,305,470 A | 4/1994 | McKay |
| 5,305,471 A | 4/1994 | Steele et al. |
| 5,322,061 A | 6/1994 | Brunson |
| 5,366,492 A | 11/1994 | Ueki |
| 5,378,225 A | 1/1995 | Chatman et al. |
| 5,383,869 A | 1/1995 | Osborn, III |
| 5,395,399 A | 3/1995 | Rosenwald |
| 5,395,400 A | 3/1995 | Stafford et al. |
| 5,398,667 A | 3/1995 | Witt |
| 5,415,650 A | 5/1995 | Sigl |
| 5,484,366 A | 1/1996 | Wilkinson |
| 5,484,448 A | 1/1996 | Steele et al. |
| 5,496,357 A | 3/1996 | Jensen et al. |
| 5,496,358 A | 3/1996 | Rosenwald |
| 5,503,908 A | 4/1996 | Faass |
| 5,534,021 A | 7/1996 | Dvoretzky et al. |
| 5,540,976 A | 7/1996 | Shawver et al. |
| 5,553,608 A | 9/1996 | Reese et al. |
| 5,562,648 A | 10/1996 | Peterson |
| 5,575,786 A | 11/1996 | Osborn, III |
| 5,605,144 A | 2/1997 | Simmons et al. |
| 5,628,308 A | 5/1997 | Harges, Jr. et al. |
| 5,671,615 A | 9/1997 | Kjaergaard et al. |
| 5,674,216 A | 10/1997 | Buell et al. |
| 5,674,270 A | 10/1997 | Viltro et al. |
| 5,687,587 A | 11/1997 | Michel |
| 5,690,627 A | 11/1997 | Clear et al. |
| 5,699,791 A | 12/1997 | Sukienniki et al. |
| 5,717,991 A | 2/1998 | Nozaki et al. |
| 5,728,058 A | 3/1998 | Ouellette et al. |
| 5,728,146 A | 3/1998 | Burkett et al. |
| 5,735,807 A | 4/1998 | Cropper |
| 5,735,889 A | 4/1998 | Burkett et al. |
| 5,741,318 A | 4/1998 | Ouellette et al. |
| 5,766,235 A | 6/1998 | Kostopoulos |
| 5,774,338 A | 6/1998 | Wessling, III |
| 5,782,819 A | 7/1998 | Tanzer et al. |
| 5,807,267 A | 9/1998 | Bryars et al. |
| 5,817,584 A | 10/1998 | Singer et al. |
| 5,845,340 A | 12/1998 | Frislie |
| 5,860,945 A | 1/1999 | Cramer et al. |
| 5,890,636 A | 4/1999 | Kibbe |
| 5,904,710 A | 5/1999 | Davis et al. |
| 5,906,637 A | 5/1999 | Davis et al. |
| 5,918,590 A | 7/1999 | Burkett et al. |
| 5,925,072 A | 7/1999 | Cramer et al. |
| 5,928,275 A | 7/1999 | Yates et al. |
| 5,934,275 A | 8/1999 | Gazzara |
| 5,938,089 A | 8/1999 | Abreu-Marston |
| 5,980,562 A | 11/1999 | Ouellette et al. |
| 5,994,612 A | 11/1999 | Watkins |
| 6,019,782 A | 2/2000 | Davis et al. |
| 6,020,040 A | 2/2000 | Cramer et al. |
| 6,048,326 A | 4/2000 | Davis et al. |
| 6,074,413 A | 6/2000 | Davis et al. |
| 6,096,067 A | 8/2000 | Cramer et al. |
| 6,102,937 A | 8/2000 | Cramer et al. |
| 6,109,496 A | 8/2000 | Andrew et al. |
| 6,120,485 A | 9/2000 | Gustafsson et al. |
| 6,123,717 A | 9/2000 | Davis et al. |
| 6,137,675 A | 10/2000 | Perkins |
| 6,146,732 A | 11/2000 | Davis et al. |
| 6,148,817 A | 11/2000 | Bryant et al. |
| 6,183,458 B1 | 2/2001 | Ahlstrand et al. |
| 6,186,969 B1 | 2/2001 | Bell et al. |
| 6,189,149 B1 | 2/2001 | Allen |
| 6,336,935 B1 | 1/2002 | Davis et al. |
| 6,338,340 B1 | 1/2002 | Finch et al. |
| 6,340,472 B1 | 1/2002 | Zhang et al. |
| 6,345,751 B1 | 2/2002 | Elliot |
| 6,346,097 B1 | 2/2002 | Blaney |
| 6,367,088 B1 | 4/2002 | Bergemann |
| 6,375,646 B1 | 4/2002 | Widlund et al. |
| 6,393,621 B1 | 5/2002 | Redwine et al. |
| 6,436,020 B1 | 8/2002 | Weingand |
| 6,440,159 B1 | 8/2002 | Edwards et al. |
| 6,465,006 B1 | 10/2002 | Zhang et al. |
| 6,488,959 B2 | 12/2002 | Stanley et al. |
| 6,516,289 B2 | 2/2003 | David |
| 6,546,281 B1 | 4/2003 | Zhang et al. |
| 6,570,053 B2 | 5/2003 | Roe et al. |
| 6,584,976 B2 | 7/2003 | Japuntich et al. |

| | | |
|---|---|---|
| 6,605,071 B1 | 8/2003 | Gray et al. |
| 6,613,350 B1 | 9/2003 | Zhang et al. |
| 6,615,838 B1 | 9/2003 | Tsai |
| 6,616,649 B1 | 9/2003 | Ismail |
| 6,632,212 B1 | 10/2003 | Morman et al. |
| 6,644,314 B1 | 11/2003 | Eisberg |
| 6,656,210 B1 | 12/2003 | Plewes |
| 6,698,636 B2 | 3/2004 | Angus et al. |
| 6,702,801 B2 | 3/2004 | VanGompel et al. |
| 6,713,660 B1 | 3/2004 | Roe et al. |
| 6,726,668 B2 | 4/2004 | Underhill et al. |
| 6,726,673 B1 | 4/2004 | Zhang et al. |
| 6,770,064 B1 | 8/2004 | Ruscher |
| 6,780,426 B2 | 8/2004 | Zhang et al. |
| 6,893,453 B2 | 5/2005 | Agarwal et al. |
| 6,899,257 B2 | 5/2005 | Jones |
| 6,928,657 B2 | 8/2005 | Bell et al. |
| 6,929,617 B2 | 8/2005 | McCormick et al. |
| 6,931,875 B1 | 8/2005 | Allen et al. |
| 6,936,018 B2 | 8/2005 | Chalek |
| 6,969,378 B1 | 11/2005 | Vukos et al. |
| 7,018,368 B2 | 3/2006 | VanGompel et al. |
| 7,056,411 B2 | 6/2006 | Desai et al. |
| 7,223,818 B2 | 5/2007 | Autran et al. |
| 7,273,476 B2 | 9/2007 | Mueller et al. |
| 7,458,961 B2 | 12/2008 | Carstens |
| 7,462,173 B2 | 12/2008 | Carstens |
| 7,481,801 B2 | 1/2009 | Carstens |
| 7,537,587 B2 | 5/2009 | Carstens |
| 7,614,399 B2 | 11/2009 | Carstens |
| 7,785,311 B2 | 8/2010 | Carstens |
| 7,789,867 B2 | 9/2010 | Carstens |
| 2001/0025140 A1 | 9/2001 | Torok et al. |
| 2002/0023284 A1 | 2/2002 | Tito |
| 2004/0031830 A1 | 2/2004 | Kay |
| 2004/0094592 A1 | 5/2004 | Brown |
| 2004/0127881 A1 | 7/2004 | Stevens et al. |
| 2004/0193133 A1 | 9/2004 | Desai et al. |
| 2004/0210287 A1 | 10/2004 | Greene |
| 2005/0049661 A1 | 3/2005 | Koffroth |
| 2005/0090795 A1 | 4/2005 | Coleman |
| 2005/0193476 A1 | 9/2005 | Chinn |
| 2005/0255898 A1 | 11/2005 | Huang |
| 2006/0004342 A1 | 1/2006 | Sawyer et al. |
| 2006/0010578 A1 | 1/2006 | Kane |
| 2006/0069319 A1 | 3/2006 | Elhag et al. |
| 2006/0117458 A1 | 6/2006 | Ishihara et al. |
| 2006/0253093 A1 | 11/2006 | Beck et al. |
| 2006/0264865 A1 | 11/2006 | Carstens |
| 2006/0264867 A1 | 11/2006 | Carstens |
| 2006/0264868 A1 | 11/2006 | Carstens |
| 2006/0264869 A1 | 11/2006 | Carstens |
| 2006/0264870 A1 | 11/2006 | Carstens |
| 2006/0264871 A1 | 11/2006 | Carstens |
| 2006/0264872 A1 | 11/2006 | Carstens |
| 2006/0264873 A1 | 11/2006 | Carstens |
| 2006/0264874 A1 | 11/2006 | Carstens |
| 2006/0264877 A1 | 11/2006 | Carstens |
| 2006/0264878 A1 | 11/2006 | Carstens |
| 2006/0264879 A1 | 11/2006 | Carstens |
| 2006/0264880 A1 | 11/2006 | Carstens |
| 2006/0264881 A1 | 11/2006 | Carstens |
| 2006/0264882 A1 | 11/2006 | Carstens |
| 2006/0264883 A1 | 11/2006 | Carstens |
| 2006/0264884 A1 | 11/2006 | Carstens |
| 2006/0264885 A1 | 11/2006 | Carstens |
| 2007/0093771 A1 | 4/2007 | Aritzi et al. |
| 2007/0102461 A1 | 5/2007 | Carstens |
| 2007/0106237 A1 | 5/2007 | Carstens |
| 2007/0106242 A1 | 5/2007 | Carstens |
| 2007/0106350 A1 | 5/2007 | Carstens |
| 2007/0106352 A1 | 5/2007 | Carstens |
| 2007/0106353 A1 | 5/2007 | Carstens |
| 2007/0106354 A1 | 5/2007 | Carstens |
| 2007/0106355 A1 | 5/2007 | Carstens |
| 2007/0106356 A1 | 5/2007 | Carstens |
| 2007/0139875 A1 | 6/2007 | Carstens |
| 2007/0142816 A1 | 6/2007 | Carstens |
| 2007/0287348 A1 | 12/2007 | Autran et al. |
| 2007/0299489 A1 | 12/2007 | Francis et al. |
| 2008/0119813 A1 | 5/2008 | Carstens |
| 2008/0119815 A1 | 5/2008 | Carstens |
| 2009/0030392 A1 | 1/2009 | Kanai et al. |
| 2010/0094240 A9 | 4/2010 | Desai et al. |

OTHER PUBLICATIONS

Labels on package for product: Therma Care™ Heatwraps (Neck to Arm), Procter & Gamble, marketed prior to Nov. 2004.
Labels on package for product: Walgreens HeatWraps (Back/Hip), Dist. By Walgreen Company, marketed prior to Nov. 2005.
Labels on package for product: Universal Plus Hot & Cold Compress (Reusable), Bar Code/SKU 7-75965-22100.4, Medi-Temp, LLC, marketed prior to Nov. 2005.
Labels on package for product: Polar-Preene™ I.C.E./Heat (Adjustable/Reusable) (Back/Shoulder Wrap), Bar Code/SKU 3-8290-486909-0, BD Consumer Healthcare, marketed prior to Nov. 2005.
Labels on package for product: HeatWraps, Lot: 407092, Dist. By Perrigo, marketed prior to Nov. 2005.
Labels on package for product: IcyHot® Medicated Sleeve (ankle, elbow, wrist & knee), Bar Code/SKU 0-41167-08304-8, Dist. By Chattem, Inc., marketed prior to Nov. 2004.
Labels on package for product: Well Patch™ Heat Warming Pads (back), Bar Code/SKU 3-10742-09850-1, Dist. By The Mentholatum Co., Inc., marketed prior to Nov. 2005.
Labels on package for product: Grabber® Mycoal™ Heat Treat® Body Warmer, Dist. By Grabber, marketed prior to Nov. 2005.
U.S. Appl. No. 11/135,013, filed May 23, 2005, Carstens.
U.S. Appl. No. 11/135,034, filed May 23, 2005, Carstens.
U.S. Appl. No. 11/135,016, filed May 23, 2005, Carstens.
U.S. Appl. No. 11/135,019, filed May 23, 2005, Carstens.
U.S. Appl. No. 11/135,020, filed May 23, 2005, Carstens.
U.S. Appl. No. 11/135,015, filed May 23, 2005, Carstens.
U.S. Appl. No. 11/135,024, filed May 23, 2005, Carstens.
U.S. Appl. No. 11/135,025, filed May 23, 2005, Carstens.
U.S. Appl. No. 11/135,026, filed May 23, 2005, Carstens.
U.S. Appl. No. 11/135,027, filed May 23, 2005, Carstens.
U.S. Appl. No. 11/135,031, filed May 23, 2005, Carstens.
U.S. Appl. No. 11/135,014, filed May 23, 2005, Carstens.
U.S. Appl. No. 11/135,023, filed May 23, 2005, Carstens.
U.S. Appl. No. 11/135,033, filed May 23, 2005, Carstens.
U.S. Appl. No. 11/135,021, filed May 23, 2005, Carstens.
U.S. Appl. No. 11/135,022, filed May 23, 2005, Carstens.
U.S. Appl. No. 11/135,030, filed May 23, 2005, Carstens.
U.S. Appl. No. 11/135,029, filed May 23, 2005, Carstens.
U.S. Appl. No. 11/135,017, filed May 23, 2005, Carstens.
U.S. Appl. No. 11/135,028, filed May 23, 2005, Carstens.
U.S. Appl. No. 11/135,018, filed May 23, 2005, Carstens.
U.S. Appl. No. 11/135,032, filed May 23, 2005, Carstens.
U.S. Appl. No. 11/311,773, filed Dec. 19, 2005, Carstens.
U.S. Appl. No. 11/269,267, filed Nov. 8, 2005, Carstens.
U.S. Appl. No. 11/269,268, filed Nov. 8, 2005, Carstens.
U.S. Appl. No. 11/269,269, filed Nov. 8, 2005, Carstens.
U.S. Appl. No. 11/269,270, filed Nov. 8, 2005, Carstens.
U.S. Appl. No. 11/269,254, filed Nov. 8, 2005, Carstens.
U.S. Appl. No. 11/269,255, filed Nov. 8, 2005, Carstens.
U.S. Appl. No. 11/269,256, filed Nov. 8, 2005, Carstens.
U.S. Appl. No. 11/269,252, filed Nov. 8, 2005, Carstens.
U.S. Appl. No. 11/269,253, filed Nov. 8, 2005, Carstens.
U.S. Appl. No. 11/269,266, filed Nov. 8, 2005, Carstens.
U.S. Appl. No. 11/311,774, filed Dec. 19, 2005, Carstens.
Carstens, U.S. Appl. No. 12/870,212, filed Aug. 27, 2010, Pending.
Carstens, U.S. Appl. No. 12/871,521, filed Aug. 30, 2010, Pending.
Carstens, U.S. Appl. No. 12/870,234, filed Aug. 27, 2010, Pending.

BODY CONFORMING TEXTILE HOLDER AND ABSORBENT ARTICLE

FIELD OF THE INVENTION

The present invention relates to a body conforming, reusable, washable, textile holder for removably holding at least one article in close bodily contact. More particularly, the invention relates to a reusable wrap or tube holder constructed to enclose a portion of the body where the article is to be held. The article may be a therapeutic article, such as a heat generating thermal pack, a cooling pack, or other article comprising a therapeutic agent; an absorbent article; a sensing article; or a filter article. The invention also relates to a system comprising the body conforming holder and an article for use therewith, and a method for holding such an article in close bodily contact by wearing the holder.

BACKGROUND OF THE INVENTION

A common method of treating acute, recurrent, and chronic pain is by the topical application of heat to the afflicted area. Such heat treatments are used as therapy for aches, stiffness in muscles and joints, nerve pain, rheumatism and the like. The method for relieving pain often involves topically applying a relatively high heat, e.g., greater than about 40° C., for a short period of time, such as from about twenty minutes to about one hour.

Combinations of elastic wraps and heating pads are available for treating pain. Many of these combination devices use hot water bottles, hot packs, and the like, and are reusable by heating the contents, such as water and/or microwaveable gels. Many such heating devices that require the thermal source to be replenished are inconvenient to use on a regular or extended basis. Further, the heat energy may not be immediately available when needed or released in a controllable manner. Such thermal devices may not provide long lasting heat or maintain a consistent temperature over long periods of time. Proper positioning of the thermal source also may not be maintainable during use. The therapeutic effects from the administration of heat diminish after the heat source is removed.

Disposable heat packs based on iron oxidation, such as those described in U.S. Pat. Nos. 4,366,804, 4,649,895, 5,046,479 and U.S. Pat. No. Re. 32,026, are known. However, many of these devices are bulky, cannot maintain a consistent and controlled temperature, have difficulty staying in place during use, and/or have unsatisfactory physical dimensions that hinder their effectiveness. Such devices cannot be easily incorporated into wrap or tube holders that comfortably conform to various body contours. The devices may thus not deliver consistent, convenient and/or comfortable heat application to the body.

U.S. Pat. No. 6,074,413, Davis, et al., discloses that maintaining a sustained skin temperature of from about 32° C. to about 42° C. for a period of greater than about one hour substantially relieves acute, recurrent, and/or chronic pain, including skeletal, muscular, and back pain, and substantially prolongs relief even after the heat source is removed from the body. The patent discloses disposable elastic thermal wraps comprising one or more thermal packs having a plurality of heat cells spaced apart and fixed within or to the structure of the thermal pack. While such disposable elastic thermal wraps can be efficacious, they are designed for single use and can be relatively expensive.

Thus, there is a continuing need for a more convenient, comfortable, reliable and cost effective holder for holding therapeutic and other articles in close bodily contact.

SUMMARY OF THE INVENTION

The present invention relates to an absorbent system comprising:
a) a body conforming, reusable, washable, textile holder for removably holding at least one absorbent article in close bodily contact, said holder being a wrap or tube constructed to enclose a portion of the body where the absorbent article is to be held, and comprising an elastic region having a Holding Force (HF-4.0) of greater than about 0.1 kgf and a Holding Force (HF-2.5) of less than about 1.0 kgf; and
b) at least one absorbent article capable of being removably held in close bodily contact by said holder, said article comprising a liquid pervious body facing side, a liquid impervious side opposite the body facing side, and an absorbent component between the liquid pervious side and the liquid impervious side, wherein the liquid pervious side and the liquid impervious side are arranged to form a unitary structure.

The invention also relates to a system as described above wherein the holder is a wrap comprising at least two cooperating fastening materials affixed to opposed surfaces of the holder that can be positioned to removably enclose a portion of the body where the absorbent article is to be held.

In another aspect, the invention relates to a system as described above wherein the holder is a tube that can be positioned to enclose a portion of the body where the absorbent article is to be held.

DETAILED DESCRIPTION OF THE INVENTION

Figure 1:
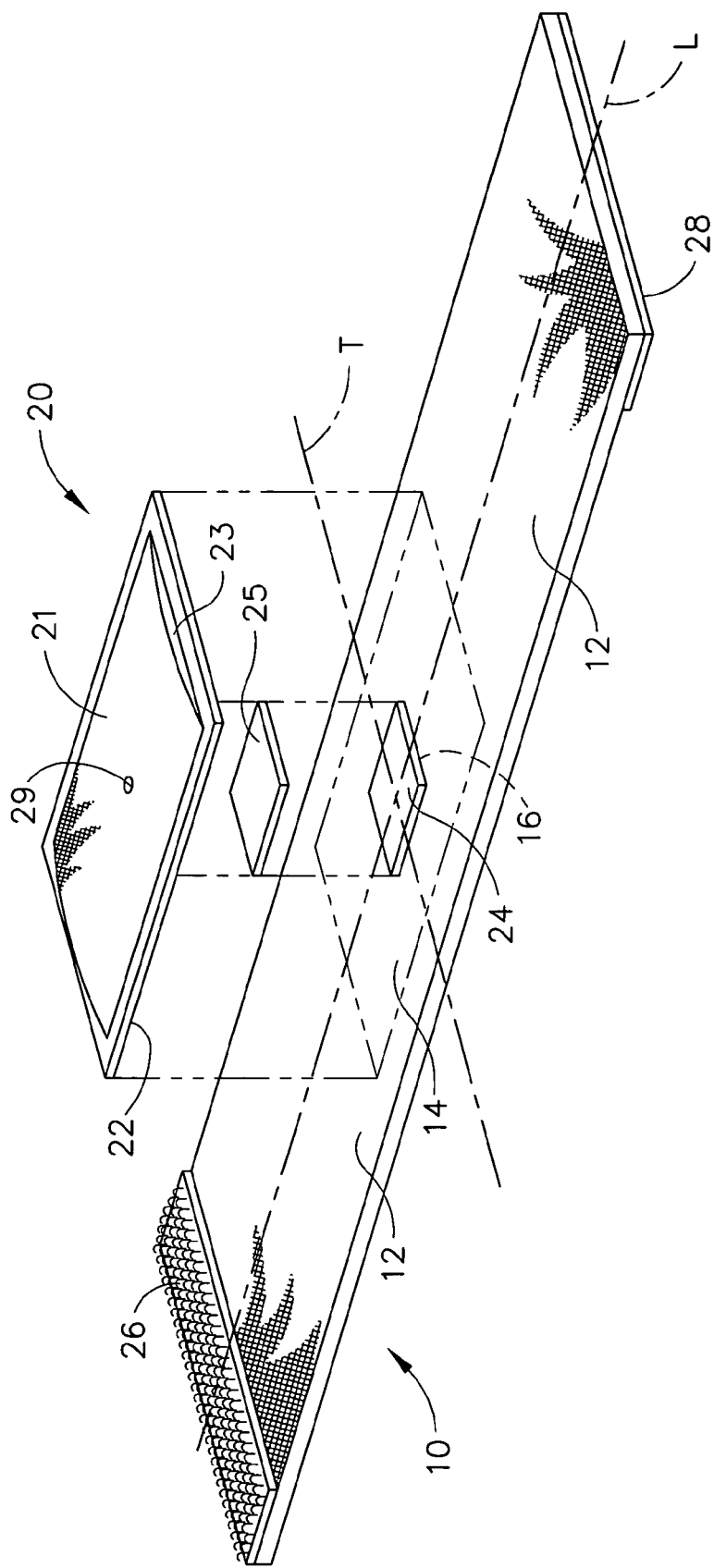
FIG. 1 is a perspective view of a holder and system of the invention comprising a body conforming textile wrap holder and an article capable of being removably held in close bodily contact by the holder.

The reusable, washable, textile holder of the invention is suitable for removably holding one or more coordinated articles in close bodily contact in a desired position or location on the body of a user. In one embodiment, the body conforming holder removably holds one or more replaceable, disposable heat generating thermal packs in close bodily contact against a specific area of the user's body for pain relief or thermal comfort. The holder can be reused with a new article (e.g., thermal pack) affixed to the holder when needed. As a result, the system comprising the holder and article can provide a desired level of efficacy (e.g., heat) for a period of time, with a new article mounted to the holder whenever extended or repeated exposure time is desired. In another embodiment, the holder is intended for use with a therapeutic article comprising a therapeutic agent that can be delivered to a location on the body in need of therapeutic treatment. In another embodiment, the holder removably holds an absorbent article in close bodily contact, such as for wound care. In still another embodiment, the holder is a face mask intended for use with a filter article to filter out objectionable contaminants. The holder may also be used to removably hold a sensing article having a sensor operatively connected to the article in close bodily contact. The holder and article system can thus provide effective and efficient heat or therapeutic agent transfer, wound care, filtering or sensing by holding and maintaining the article in close bodily contact.

A reusable holder/replaceable thermal pack system herein can be used for relieving pain in various places on the body, including lower back pain, arm or leg pain, e.g., in the thigh, knee, forearm, etc., and neck and shoulder pain. In another embodiment, the reusable holder/replaceable thermal pack system can be used for improving thermal comfort by heating various body regions, including the center or core of the body, hands, feet, or head, etc. Alternatively, the holder can be used with a cooling article to provide cooling to the body. The holder can also be used with an article that delivers a therapeutic agent, such as an aromatic compound, a pharmaceutical active, a lotion, an emollient, a moisturizing agent, or mixtures thereof, to the body. The reusable holders and replaceable articles herein are coordinated so as to have compatible shapes, sizes, and flexibility in order to fit reliably and comfortably against the body region where thermal, therapeutic or other benefit is desired.

While not intending to be limited by theory, it is believed that the elastic properties of the textile holder provide sufficient holding force to hold the article (e.g., a thermal pack) in close bodily contact throughout a range of wearer motions. This sufficient, comfortable and reliable holding force often results in improved therapeutic activity or other performance benefits (e.g., more consistent heat transfer for more effective pain relief). Additionally, when the reusable holder and removable article are designed and coordinated to work together, the resulting system can be optimized to provide consumer benefits such as more effective heat transfer to more body areas, improved wearing comfort, discreetness under clothing, better stay-in-place performance, and/or better cost effectiveness.

The invention thus also relates to a system comprising a reusable, body conforming holder and at least one coordinated article for use therewith, for example, a therapeutic delivery system, a heat delivery system, an absorbent system, a sensing system or a filtering system. The invention also relates to a method for holding such an article in close bodily contact in a specific body region by wearing the holder. The article has a size and shape compatible with the holder, and is capable of being held in close bodily contact in the desired body region by the holder. Typically, the article and the holder are designed and coordinated to work together. As a result, the system provides improved performance (e.g., heat transfer and pain relief) and better wearing comfort and discreetness. For example, the heat delivery system of the invention adapts to a wide variety of body contours, and provides consistent, convenient, and comfortable heat application. The article and holder of this system may be packaged in a common, bundled, coordinated, or associated package or packages, and may be sold as a kit, for example a pain relief kit. The articles may also be sold separately from the holder. Typically, replacement articles are sold separately from the holder, with or without instructions for use with the holder.

As used herein, the term "thermal pack" refers to a heating article that is placed against or in proximity to the body in a specific region to transfer heat to the user's body for pain relief or thermal comfort. The term "thermal pack" is intended to include various heat providing articles, including thermal pack formulations and constructions described in U.S. Pat. No. 6,146,732, Davis, et al.; U.S. Pat. No. 6,074,413, Davis, et al.; U.S. Pat. No. 6,336,935, Davis et al; and U.S. Pat. No. 6,020,040, Cramer et al.; all incorporated herein by reference. Thermal packs typically comprise one or more heat cells comprising an exothermic composition fixedly attached to the thermal pack.

The term "heat cell" refers to a unified structure comprising an exothermic composition, typically having specific iron oxidation chemistry, enclosed within at least two layers. At least one layer may be oxygen permeable, capable of providing long lasting heat generation with temperature control, and have specific physical dimensions and fill characteristics, such as described in U.S. Pat. No. 5,918,590, Burkett, et al., incorporated herein by reference. Typically, these heat cells are fixedly attached to the thermal pack.

The term "disposable" refers to articles that are intended to be discarded after a single use or a few uses (i.e., they are not intended to be restored and/or reused after the article has been fully expended). Such structures may be recycled, composted or otherwise disposed of in an environmentally compatible manner.

The term "reusable" refers to articles, such as the holders herein, intended to be reused. The articles may be cleaned, laundered or otherwise restored and/or reused after use.

The reusable holder/disposable article system of the present invention may comprise one or more articles mounted to the holder at the same time. However, for clarity, a holder/article system comprising a single article may be described herein.

The holder of this invention is comfortable to wear notwithstanding the close conformity of the holder and article to the wearer's body. It is believed that the sufficient and comfortable holding force provided by the holder is due at least in part to the force exerted by the elastic material used in the holder. The holder can be characterized as comprising an elastic region, and often more than one elastic region, with a moderate to low Holding Force (HF) value at a given extension distance when measured as described herein, and a relatively high available stretch as worn. In contrast, previous holders have often attempted to hold an article to a body area by using materials of relatively high stretch modulus that hold an article using a tight overall fit. Such high modulus holders are often characterized as having high contractive forces, relatively low available stretch, and stretch properties in only one direction. Holders of these types generally have high Holding Force values at a given extension distance, and are often described as uncomfortable or are unable to maintain the article in close bodily contact, especially with body motion.

The elastic region of the holder herein cooperates with other regions so that the holder as worn provides a comfortable but sufficient holding force to hold the article against the body. Without being bound by theory, it is believed that the holding force provided by the holder is due at least in part to the compressive holding force provided by the stretch material in the holder. When the holder is stretched in use, the material exerts compressive forces to hold the article closely against the wearer's body. This conformity is maintained over a wide range of body movement. The holding force is great enough to hold the article in close bodily contact, but generally is not great enough to cause wearer discomfort. Material of the elastic region typically has moderate to low stretch modulus and provides relatively high available stretch as worn. This high available stretch, typically in both the lateral and longitudinal directions, combined with sufficient but relatively low holding force, helps to maintain the article in close bodily contact across a range of body sizes, article sizes, and body motions.

In one embodiment, the holder comprises an elastic region having a Holding Force (HF-4.0) of greater than about 0.05 kgf, typically greater than about 0.1 kgf, as measured by the Holding Force method presented herein. In another embodiment, the holder comprises an elastic region having a Holding Force (HF-4.0) of greater than about 0.2 kgf, typically greater than about 0.3 kgf. The elastic region typically also has a Holding Force (HF-1.0) of less than about 1.0 kgf. The elastic region typically has a Holding Force (HF-2.0) of less than about 1.0 kgf, and typically has a Holding Force (HF-3.0) of less than about 1.0 kgf. In one embodiment, the holder comprises an elastic region having a Holding Force (HF-4.0) of less than about 1.0 kgf, and typically having a Holding Force (HF-5.0) of less than about 1.0 kgf, more typically less than about 0.8 kgf. In another embodiment, the holder comprises an elastic region having a Holding Force (HF-5.5) of less than about 1.0 kgf, more typically less than about 0.8 kgf.

The elastic region of the holder can comprise any woven material, knit material, nonwoven material (with stretch incorporated as known in the art), or the like that possesses the requisite physical properties. Similarly, the holder can comprise one material or a combination of materials, stitching, and/or design patterns that collectively possess the requisite physical properties. The elastic region can be cut to an appropriate shape and size, and joined to the remaining portions of the holder. In one embodiment, the elastic region of the holder is wholly plain knit, typically jersey knit, from a combination of elastically extensible and non-elastically extensible yarns. The elastic properties of the individual yarns and the particular knitting pattern can be used to define the mechanical properties of the holder. The holder typically comprises knit material and elastomeric fiber material. In one embodiment, the holder comprises wholly plain knit, e.g., jersey knit, using elastomeric fiber material such as Lycra® or spandex yarn having suitable mechanical properties in all courses. Other knitting patterns and alternative yarns can be used to provide the desired mechanical properties. Suitable yarns include natural yarns, such as cotton yarns and wool yarns, and synthetic yarns, such as nylon yarns, polyester yarns, acrylic yarns, and combinations thereof, e.g., nylon yarns and cotton yarns. Typically, elastomeric fiber material such as Lycra® or spandex yarns are used with these natural and/or synthetic fibers to provide the desired stretch properties. In one embodiment, the elastic region of the holder comprises from about 5% to about 30%, typically from about 10% to about 25%, more typically from about 15% to about 20%, of the elastomeric fiber material, e.g., Lycra®. For example, the elastic region of the holder may comprise from about 80% to about 85% nylon yarn and from about 15% to about 20% of Lycra®.

While the article attachment region of the holder need not comprise an elastic material, it is typically extensible in both the longitudinal and lateral directions. Such elastic extensibility enables the holder to fit a variety of bodily shapes and sizes and provides good conformity to a wearer's body. The mounting region and article attachment region cooperate with the elastic region of the holder to provide sufficient holding force to hold the article in close bodily contact throughout a range of wearer movements. Such a force helps maintain the article worn with the holder in close bodily contact. In one embodiment, the elastic region(s), mounting region(s), and the article attachment region(s) of the holder are made of the same material, typically a knit material as described above. The holder may comprise at least one additional extension, panel, or other structure extending beyond or attached to the above regions so long as it does not significantly interfere with the function of the holder.

While the present invention encompasses a wide variety of holder designs to fit various regions of the body with coordinated articles, it will often be described in terms of a holder comprising a material of relatively high stretch and moderate to low stretch modulus, used in conjunction with an article such as a therapeutic article, particularly a heat generating thermal pack. FIG. 1 shows a perspective view of such a holder 10 of the invention in the form of a wrap in a full flat out position. The holder comprises elastic regions 12, a mounting region 14, and an article attachment region 16. In one embodiment, elastic regions 12 are elastic in both the lateral and longitudinal directions.

The holder 10 has a longitudinal centerline L and a lateral centerline T. The term "longitudinal" refers to a line, axis or direction in the plane of the holder that is generally elongated to accommodate fit around a body region. The term "lateral" refers to a line, axis or direction that lies within the plane of the holder that is generally perpendicular to the longitudinal direction. The elastic regions 12 are formed from a material of relatively high stretch and moderate to low stretch modulus. Such a wrap holder design could be worn around the waist region of a user to relieve lower back pain.

The holder 10 can comprise woven fabrics, knit fabrics, or special nonwoven fabrics (with stretch incorporated as known in the art), but typically comprises a knit fabric. Other materials having the requisite mechanical properties are also suitable. The holder is designed to be reusable, but typically is disposed of after a period of time (e.g., about 4 to 8 months depending on the amount of use) when it begins to lose elasticity or otherwise shows wear. When the holder is a knit fabric, the mechanical properties of the various components can be provided by a combination of the knit pattern used for a particular component and the yarns that are used. In one embodiment, the stretch properties of the elastic regions 12 of the holder are derived from knit materials known in the art. In one example, the elastic regions 12, mounting region 14, and article attachment region 16 are wholly knit. The holder typically comprises material having a basis weight similar to conventional undergarments in order to provide a desired "sheerness". This relatively low basis weight and sheerness facilitates wearing the delivery system comfortably and discreetly under outer garments.

The holder 10 is constructed to be reused and incorporates one or more areas, such as mounting region 14, to which a replaceable article can be removably mounted. The holder can be used with a wide variety of removable, replaceable, and typically disposable articles, including articles capable of delivering therapeutic agents, heat or cooling, absorbing body discharges, filtering undesirable particles, or sensing a condition on the body. In FIG. 1, article 20 comprises a body facing side 21, a side 22 opposite the body facing side, and a component 23 located at least partially between sides 21 and 22, such as a heating, cooling or other therapeutic agent, an absorbent component, or a sensing component. The body facing side and the opposite side are typically arranged to form a unitary structure.

Article 20 is removably mounted to holder 10 by employing a hook and loop fastening system. For example, the holder may comprise a first fastening material that cooperatively engages a second fastening material on the article and enables the article to be removably affixed to the holder. In the embodiment shown in FIG. 1, loop fastener portion 24 is securely affixed to a surface of holder 10, e.g., by gluing it to the surface of the holder. Alternatively, the loop fastener portion can be an integral part of the holder. For example, the holder or a portion thereof may be made of a material that can function as a loop fastener portion, such as a knit material. Hook fastener portion 25 is securely affixed to article 20, e.g., by gluing it to the article. Article 20 can be securely, but removeably, affixed to holder 10 by engaging hook fastening portion 25 and loop fastening portion 24. In this embodiment, holder 10 is constructed to hold article 20 in a selected location. In the alternative embodiment described above where the loop fastener portion is an integral part of the holder, the article may be affixed to any suitable portion of the holder comprising the loop material. When article 20 is expended or is otherwise being replaced, a new article comprising a hook fastener portion can be mounted to the holder in the selected location or a desired position on the holder. In another embodiment, article 20 is removably affixed to holder 10 using an adhesive material. For example, pressure sensitive adhesives known in the art may be used. Cohesive-adhesive fastening systems, such as described in U.S. Pat. No. 5,415,650, Sigl, et al., incorporated herein by reference, are also suitable for use herein.

Holder 10 comprises a fastening system to enable it to be affixed to a location on the user's body in a manner that allows article 20 to overlie the desired body area. While various fastening means can be used, FIG. 1 depicts the use of a reclosable hook and loop fastening system comprising hook fastening portion 26 and loop fastening portion 28. In this embodiment, hook fastener portion 26 is mounted along an edge of holder 10, typically on the same surface to which loop fastener portion 24 is mounted. Loop fastener portion 28 is affixed to holder 10 on the opposed surface thereof. Hook and loop fastening portions 26 and 28 can be positioned to removably enclose the portion of the body in need of treatment. By employing this construction, holder 10 can be easily and securely mounted to virtually any location on the body of the user.

Once article 20 is mounted to holder 10 in the desired position, the article is placed in contact with the body area to be treated. Holder 10 can then be wrapped around that portion of the body, with the end of the holder bearing fastener portion 26 being wrapped around the body portion as the final step. The system is secured to the body by bringing the surface of fastener portion 26 into contact with the exposed surface of fastener portion 28, enabling the hook and loop fastening members to engage. The system is thus securely affixed to the body of the user with article 20 overlying the area to be treated. As will be apparent to one of ordinary skill in the art, while the components depicted in FIG. 1 are presented as simple rectangular shapes, the system can be constructed in any desired width or length or in any shape or configuration in order to be securely mounted to the desired body location.

In one embodiment, article 20 is a heating article such as a thermal pack, or a cooling article such as a cooling pack. The heating or cooling article may be any heat generating or cooling pack known in the art, and may be available in various sizes and constructions. The thermal pack typically comprises a porous pad of non-woven material incorporating chemicals that will react exothermically in the presence of oxygen. In other constructions, different chemicals are maintained in separate chambers that rupture upon use so that the chemicals are intermixed to produce the exothermic reaction. Any such exothermic pads can be employed to achieve the therapeutic heat benefit.

In another embodiment, article 20 in FIG. 1 is a therapeutic article, and component 23 is or comprises a therapeutic agent. Typically, the side 22 is liquid impervious. Both the article and the holder typically are vapor permeable, and the article is disposable. Such a therapeutic article is designed to provide the desired therapeutic benefit by delivering an effective level of therapeutic agent (e.g., heat) to the user when the article is held in close bodily contact by the holder. The therapeutic agent typically is transferable to the wearer's body, e.g., the skin, in an effective amount to provide a therapeutic benefit. The therapeutic agent may comprise an aromatic compound, a pharmaceutical active, a lotion, an emollient, a moisturizing agent, a heating agent, a cooling agent, or mixtures thereof.

In another embodiment, article 20 in FIG. 1 is an absorbent article capable of being held in close bodily contact by the holder herein. The absorbent article comprises a liquid pervious body facing side (e.g., side 21, which may be a topsheet), a liquid impervious side opposite the body facing side (e.g., side 22, which may be a backsheet), and an absorbent component located between the liquid pervious side and liquid impervious side (e.g., component 23). Such an absorbent article can be designed to meet different absorbency needs ranging from an absorbent capacity of less than about 5 grams of fluid to a capacity of more than about 10 grams of fluid, e.g., from about 0.1 to about 20, typically from about 1 to about 10, grams of fluid.

It should be understood that absorbent articles herein are not limited to structures that have the above three primary components. Absorbent articles can be provided that only have one or two of these components, or have additional components. For example, an absorbent article need not have a topsheet if the body-facing surface of the absorbent component is suitable for use as a topsheet. A liquid impervious component, such as a liquid impervious backsheet, can be joined to the other side of the absorbent component. Alternatively, an absorbent article can comprise an absorbent component that has a liquid pervious side and a liquid impervious side. The liquid impervious side can be provided by treating the surface of the absorbent component to render it liquid impervious. The liquid pervious side of the absorbent article herein is the body-facing surface of the article. The liquid pervious side typically comprises a standard nonwoven web. Suitable fibers useful for making such a nonwoven web include polyolefin and polyester fibers. The nonwoven web typically has a basis weight from about 20 to about 200 grams per square meter, e.g., from about 30 to about 100 grams per square meter.

The absorbent component may be manufactured from a wide variety of materials commonly used in absorbent articles. The absorbent component typically is adapted to have the capacity specified herein. Examples of suitable absorbent materials include comminuted wood pulp; creped cellulose wadding; meltblown fibers; synthetic fibers such as crimped polyester fibers; tissues including tissue laminates; absorbent foams; absorbent sponges; superabsorbent polymers; absorbent gelling materials; cotton cloth; or any similar material or combinations of materials. The configuration and construction of the absorbent component may also be varied. For example, the absorbent component may have varying caliper zones, e.g., it may be profiled to be thicker in the center, or it may comprise hydrophilic gradients, superabsorbent gradients, or one or more layers or structures.

The backsheet of the absorbent article herein can be any suitable flexible, liquid impervious material. Typically, the backsheet is a polyethylene film having a thickness of from about 0.013 mm to about 0.05 mm. Suitable polyethylene films are manufactured by Clopay Corporation under the designation P18-0401 and microflex 1401. Further, the backsheet may permit vapors to escape from the absorbent component (i.e., it may be breathable) while still preventing exudates from passing through the backsheet. A suitable microporous film is supplied by Exxon Chemical USA, and described in U.S. Pat. No. 4,777,073, Sheth, incorporated herein by reference.

The topsheet, the backsheet, and the absorbent component may be assembled in a variety of configurations known in the art, including layered or "sandwich" configurations. In one embodiment, the absorbent article is assembled in a sandwich construction in which the topsheet and the backsheet have length and width dimensions generally larger than those of the absorbent component. The topsheet and the backsheet typically extend beyond the edges of the absorbent component to form portions of the periphery. The body facing side and opposite side are typically arranged to form a unitary structure. Both the absorbent article and the holder typically are vapor permeable, and the article is disposable after the absorbent is usefully expended. The absorbent article may be designed specifically for wound care, or it may be designed for absorbing other body fluids, such as perspiration. In one embodiment, the absorbent article may also comprise a therapeutic agent that is transferable to the wearer's body, e.g., the skin, in an effective amount to provide a therapeutic benefit. The therapeutic agent may comprise an aromatic compound, a pharmaceutical active, a lotion, an emollient, a moisturizing agent, a heating agent, a cooling agent, or mixtures thereof. Absorbent articles useful herein are described in U.S. Pat. Nos. 5,383,869, 5,575,786, 4,950,264, and 5,009,653, Osborn III, all incorporated herein by reference.

In another embodiment, article 20 in FIG. 1 is a sensing article capable of being held in close bodily contact by the holder. The article comprises a sensor operatively connected to the article with the sensor being capable of detecting a condition on the body. For example, the sensor may be capable of detecting various target entities, including inputs that correlate to biological analytes, etc., such as described in U.S. Pat. No. 6,570,053, Roe, et al.; and U.S. Pat. No. 6,713,660, Roe, et al.; both incorporated herein by reference. The sensor may be integral with or separate from the article. Sensor input may include a change in pressure, an electrical signal, or a motion, or combinations thereof. In one embodiment, such as described in U.S. Pat. No. 6,713,660, Roe, et al., the sensor is a biosensor including at least one bio-recognition element, the biosensor being adapted to detect a target biological analyte on or about the wearer's skin. The bio-recognition element typically comprises a biologically reactive agent. The biosensor typically detects target biological analytes selected from the group consisting of pathogenic bacteria, colonic bacteria, viruses, parasites, bacterial toxins, fungi, enzymes, and combinations thereof. The biosensor may also detect target biological analytes associated with a systemic or skin health condition of the wearer prior to the onset of clinically observable symptoms of the condition and which are above a pre-defined threshold level. Both the sensing article and the holder typically are vapor permeable, and the article is disposable.

Figure 2:
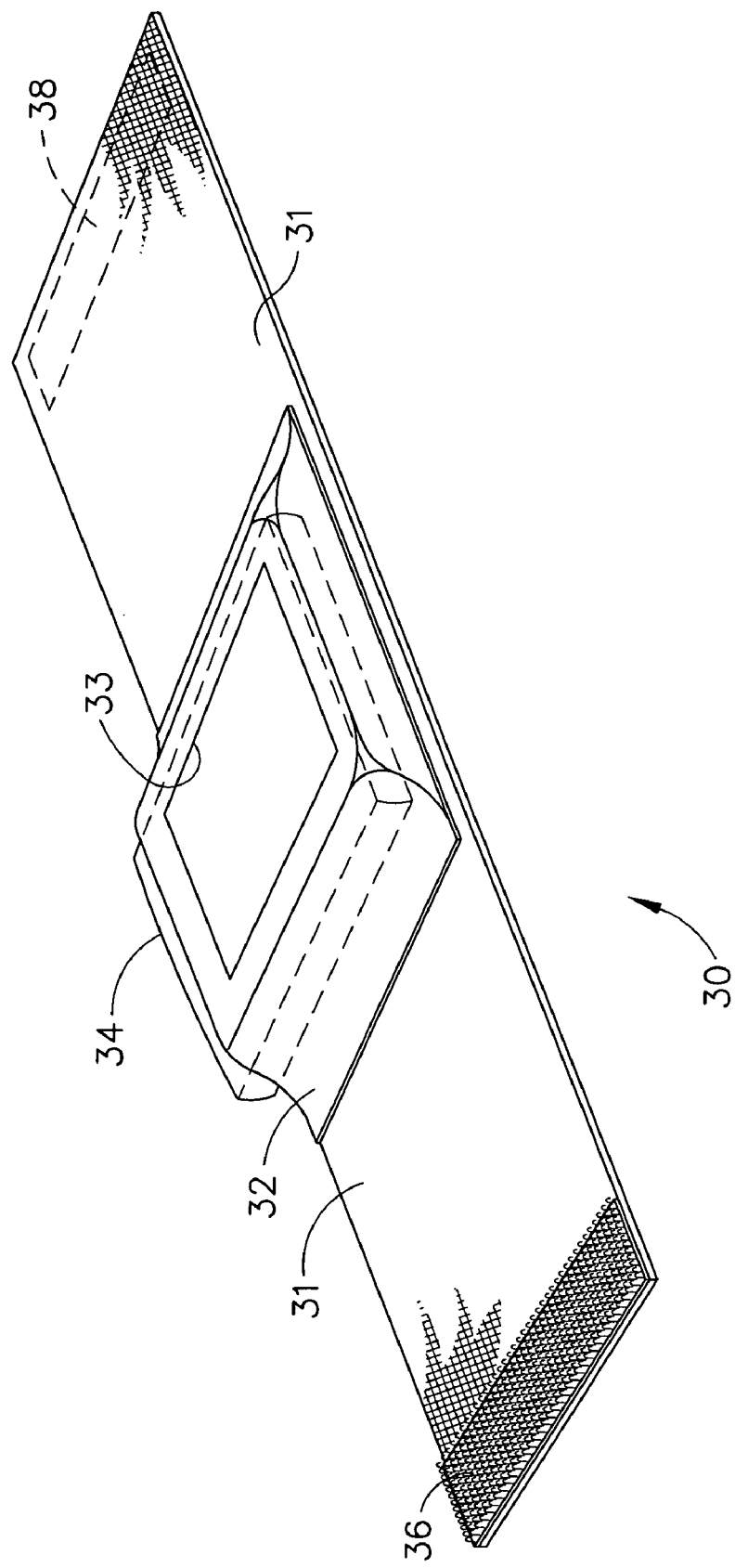
FIG. 2 is a perspective view of another holder and system of the invention comprising a body conforming textile wrap holder and an article capable of being removably held in close bodily contact by the holder.

FIG. 2 shows another method for mounting a replaceable article to a holder of the invention. The article may be a heating article, a cooling article, a therapeutic article, an absorbent article, or a sensing article, such as described above. In this embodiment, holder 30 is in the form of a wrap in a full flat out position. Holder 30 comprises elastic regions 31 and a pocket 32 affixed to the holder for receiving and supporting article 34, allowing it to be removably mounted to the holder. The pocket may be integrally formed in the holder, or it may be separately attached to the holder, e.g., by sewing, gluing or using mechanical fasteners. The pocket may have an opening, such as opening 33, or it may be made of mesh material to allow direct or substantial contact between the article and the portion of the body being treated. Alternatively, the pocket may be on the outside of the holder (the side opposite that shown in FIG. 2), and the pocket and/or the holder may have an opening therein so that the article is in direct or substantial contact with the portion of the body being treated. When article 34 is expended, it can be removed from the holder and a new article placed within the pocket. Article 34 may be secured within the pocket by the addition of a mechanical or adhesive fastening system, but typically is retained by holder 30 in the pocket simply as a result of contractive forces and friction. Alternatively, the article may be affixed to the holder by employing a mechanical or adhesive fastening system. In the embodiment shown, holder 30 also comprises hook fastener 36 and loop fastener 38 affixed to opposed surfaces of the holder that can be positioned to removably enclose a portion of the body. The holder can be secured to the body in a manner similar to that described above regarding FIG. 1.

Figure 3:
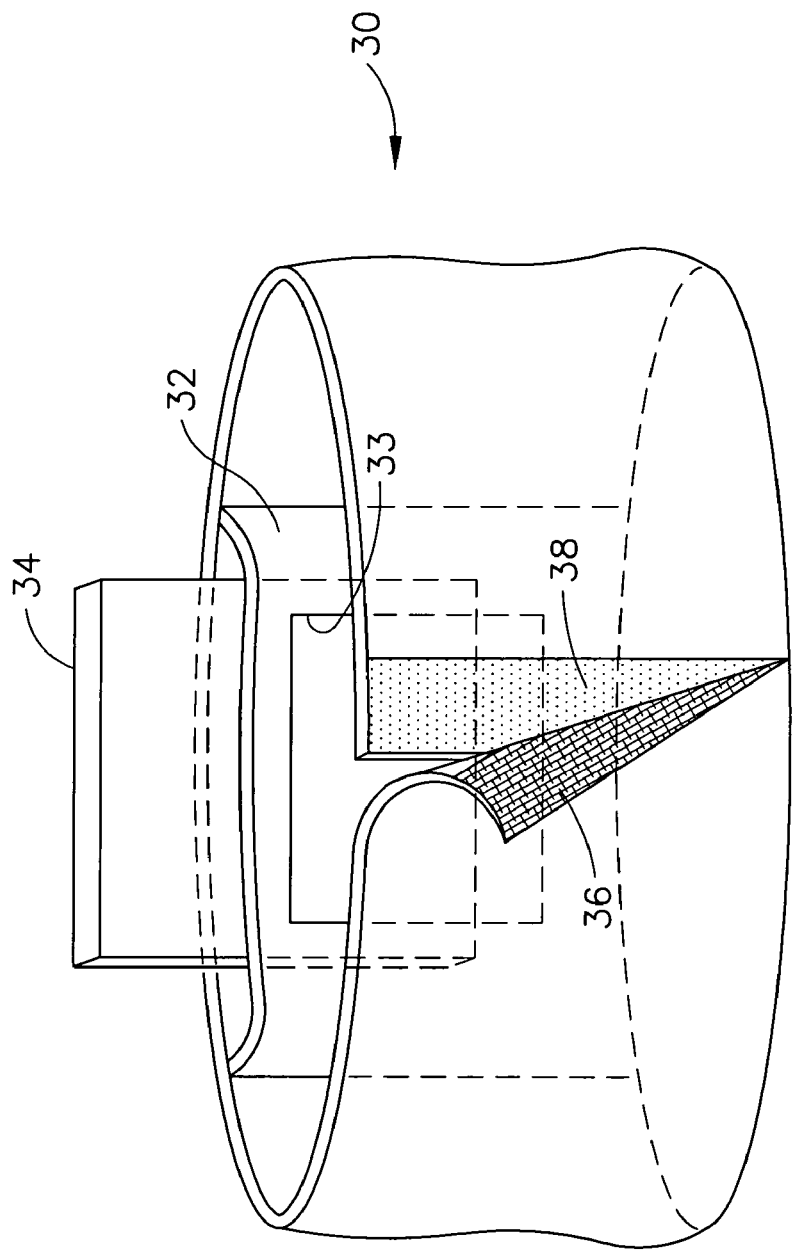
FIG. 3 is a perspective view of the holder and article shown in FIG. 2 with fastening materials partially engaged to close the holder.

FIG. 3 is a perspective view of the holder 30 and article 34 shown in FIG. 2, with hook and loop fasteners 36 and 38 partially engaged to close the holder, such as when it is placed around and removably encloses a portion of the body. Article 34 is shown partially inserted in pocket 32, but typically would by fully inserted into the pocket before the holder is closed around a portion of the body.

Figure 4:
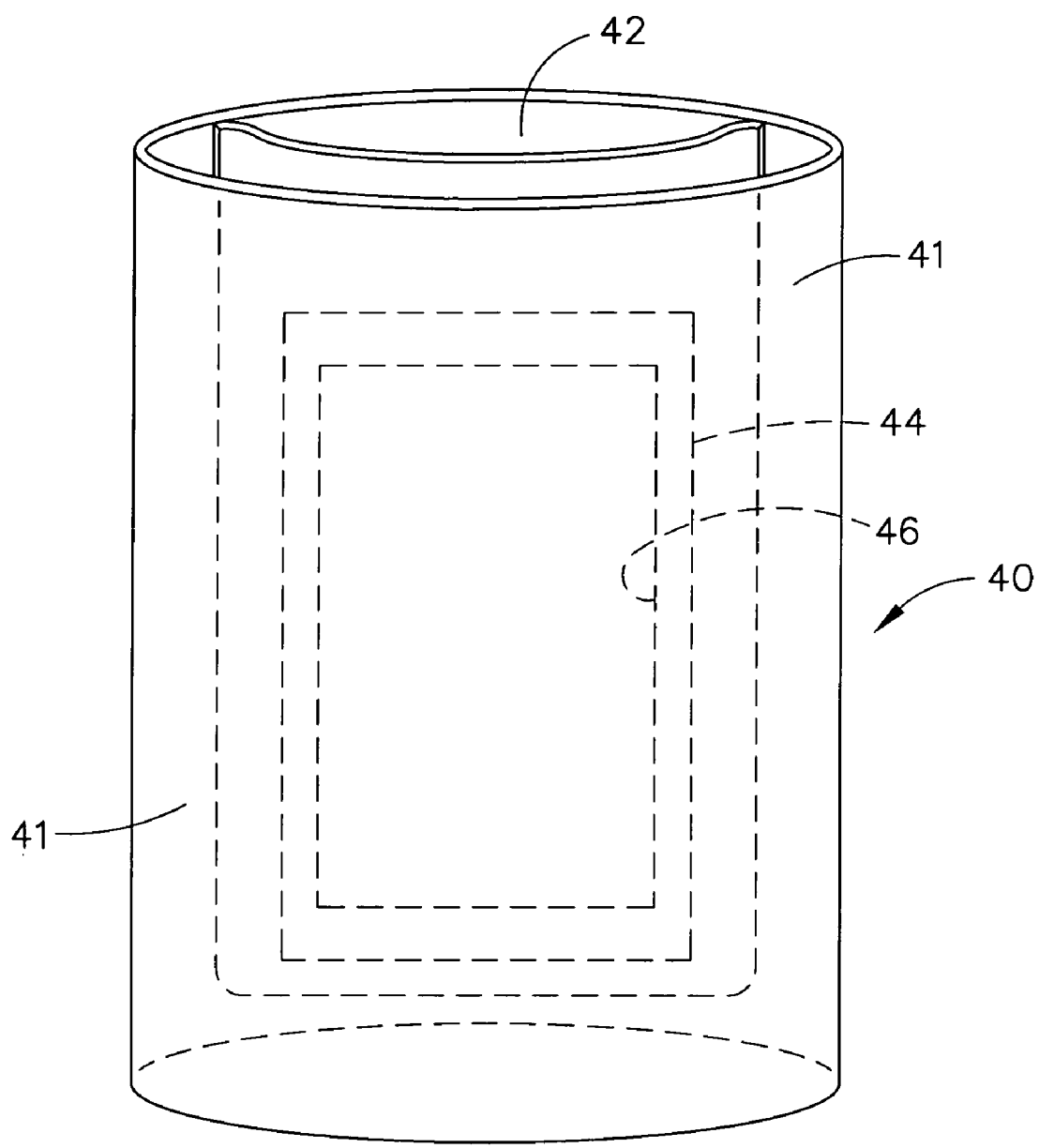
FIG. 4 is a perspective view of a holder and system of the invention comprising a body conforming textile tube holder and an article capable of being removably held in close bodily contact by the holder.

FIG. 4 illustrates another holder 40 of the invention constructed in the form of a tube that can be positioned to enclose a portion of the body where the article is to be held and removably hold the article in close bodily contact. The article may be a heating article, a cooling article, a therapeutic article, an absorbent article, or a sensing article, such as described above. Holder 40 comprises elastic regions 41 and one or more areas to which a disposable article is removably mounted. As described above, the article may be a therapeutic article, a heating article such as a thermal pack, a cooling article, an absorbent article, a sensing article, or a filter article. In one embodiment, article 44 is removably held in close bodily contact by holder 40 by inserting the article into pocket 42. As described above, the pocket may be integrally formed in the holder, or it may be separately attached to the holder, e.g., by sewing, gluing or using mechanical fasteners. The pocket may have an opening, such as opening 46, or it may be made of mesh material to allow direct or substantial contact between the article and the portion of the body being treated. Alternatively, the pocket may be on the outside of the holder, and the pocket and/or the holder may have an opening therein so that the article is in direct or substantial contact with the portion of the body being treated. Article 44 can be retained by holder 40 in the pocket simply as a result of contractive forces and friction. In another embodiment, a fastening system, such as a hook and loop fastener or an adhesive fastener, can be employed to removably mount article 44 to holder 40. Holder 40 can be formed from a circular knit elastic material of relatively high stretch and moderate to low stretch modulus. The system can be secured to the body by pulling the tube-shaped holder 40, with article 44 mounted, over the body region to be treated (e.g., leg, arm, finger, etc.).

Figure 5:
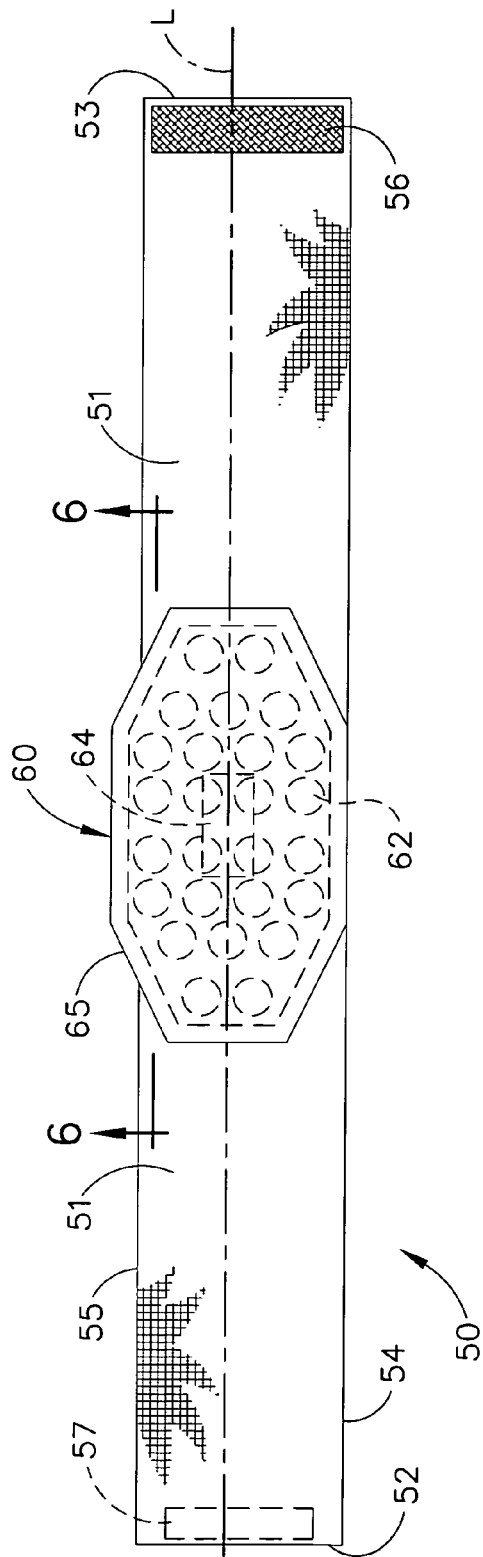
FIG. 5 is a plan view of a holder and system of the invention comprising a body conforming textile wrap holder and a thermal pack capable of being removably held in close bodily contact by the holder.

FIG. 5 shows a plan view of another holder 50 of the invention in the form of a wrap in a full flat out position. Holder 50 comprises at least one piece of flexible material, typically having a substantially rectangular shape, such as flexible material 51, having a longitudinal axis L. In one embodiment, flexible material 51 comprises an elastic region as described above. Flexible material 51 has a first end 52 and a second end 53 and at least one such elastic region therebetween capable of being stretched along longitudinal axis L. Flexible material 51 also has a first edge 54 and an opposing second edge 55, with both edges extending from first end 52 to second end 53. Flexible material 51 further has a length, when in a relaxed or stretched state, as measured in a direction parallel to longitudinal axis L from first end 52 to second end 53 that is great enough to encircle a user's body, typically the user's torso (e.g., waist), hip, upper arm, lower arm, upper leg, or lower leg, such that first end 52 overlaps second end 53. In one embodiment, holder 50 is an elastic thermal back wrap.

In FIG. 5, a heating article such as thermal pack 60 is removably mounted to holder 50 by employing a fastening system 64, such as a hook and loop mechanical fastening system or an adhesive fastening system. In one embodiment, a loop fastener portion is securely affixed to a surface of holder 50, e.g., by gluing it to the surface of the holder, while a hook fastener portion is securely affixed to thermal pack 60, e.g., by gluing it to the thermal pack. Alternatively, the loop fastener portion can be an integral part of the holder. For example, the holder or a portion thereof may be made of a material that can function as a loop fastener portion, such as a knit material. Thermal pack 60 can be securely, but removeably, affixed to holder 50 by engaging fastening system 64, such as a hook and loop mechanical fastening system or an adhesive fastening system. In this embodiment, holder 50 is constructed to hold thermal pack 60 in a selected location. In the alternative embodiment described above where the loop fastener portion is an integral part of the holder, the article may be affixed to any suitable portion of the holder comprising the loop material. When thermal pack 60 is expended, a new thermal pack comprising a hook fastener portion can be mounted to the holder in the selected location or desired position on the holder. In another embodiment, the thermal pack can be removably mounted to the holder by placing the thermal pack within a pocket on the holder. The thermal pack can also be removably affixed to the holder using an adhesive material, such as a pressure sensitive adhesive or a cohesive-adhesive fastening system as described in above.

Holder 50 comprises a fastening system to enable it to be affixed to a location on the user's body in a manner that holds thermal pack 60 over the desired body area and effectively employ the heat therapy provided by the thermal pack. While various fastening means can be used, FIG. 5 depicts the use of a reclosable hook and loop fastening system comprising hook fastening portion 56 and loop fastening portion 57. In this embodiment, hook fastener portion 56 is mounted along an edge of holder 50, typically on the same surface to which the lower portion of fastening system 64 is mounted. Loop fastener portion 57 is affixed to holder 50 on the opposed surface thereof. Hook and loop fastening portions 56 and 57 can be positioned to removably enclose the portion of the body in need of heat treatment. By employing this construction, holder 50 can be easily and securely mounted to virtually any location on the body of the user.

Once thermal pack 60 is mounted to holder 50 in the desired position, the thermal pack is placed in contact with the body area to be treated. Holder 50 can then be wrapped around that portion of the body, with the end of the holder bearing fastener portion 56 being wrapped around the body portion as the final step. The system is secured to the body by bringing the surface of fastener portion 56 into contact with the exposed surface of fastener portion 57, enabling the hook and loop fastening members to engage. The system is thus securely affixed to the body of the user with thermal pack 60 overlying the area to be treated, delivering the desired heat directly to the pain zone. While the components depicted in FIG. 5 are presented as simple shapes, the system can be constructed in any desired width or length or in any shape or configuration in order to be securely mounted to the body location where heat therapy or thermal comfort is desired. Examples of wraps of suitable size and shape, as well as thermal packs useful herein, are disclosed in U.S. Pat. Nos. 6,074,413 and 5,925,072, both incorporated herein by reference. In one embodiment, wrap 50 is a thermal back wrap comprising a lower flap portion, such as flap portion 65 extending outwardly from second edge 55, that is intended to position heat cells such as heat cells 62 low on the back of the user.

Thermal pack 60 may be any heat generating thermal pack known in the art, and may be available in various sizes, shapes, and constructions. Many different replaceable thermal packs can be used with the holder of the invention, including those described in U.S. Pat. Nos. 4,366,804; 4,649, 895; 5,046,479; 6,146,732; and 6,074,413; all incorporated herein by reference. Such articles typically are configured to have a compatible shape and size to fit with the holder and so that the system fits effectively against a specific body region where heating is desired, e.g., the knee, elbow, neck, back, or abdomen. Typically, the thermal pack is vapor permeable and disposable after the useful heat has been expended. The invention thus provides a system comprising a body conforming holder and a compatible thermal pack for use therewith. While not intending to be limited by theory, it is believed that the system of this invention provides improved comfort or pain relief performance because the holder maintains the thermal pack in close bodily contact on the wearer, and/or the thermal pack and holder are designed to work together in a coordinated manner to provide effective and efficient heat transfer.

Figure 6:
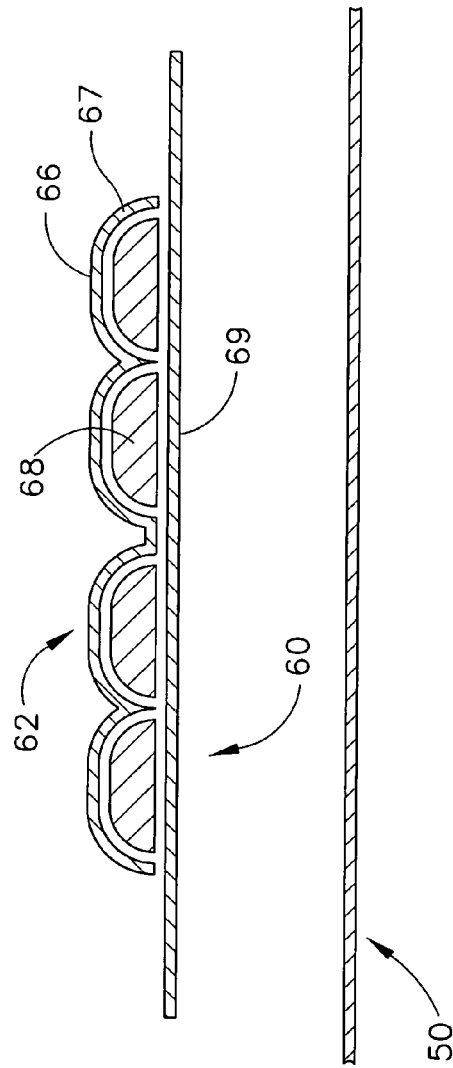
FIG. 6 is a sectional exploded view of a portion of the holder and thermal pack of FIG. 5, taken along line 6-6.

The thermal pack typically comprises one or more heat cells, such as heat cells 62, which are fixedly attached to the thermal pack. The heat cells may be arranged in a pattern such as shown in FIG. 5. Heat cells 62 apply heat energy to the user's body, such as the lower back, upper arm, lower arm, upper leg, or lower leg, when flexible material 51 is secured around the body. As shown in FIG. 6, the heat cells 62 are typically constructed by forming a pocket 66 in base material 67. Pocket 66 is then filled with an exothermic composition 68. A cover material 69 is placed over pocket 66 and heat sealed to base material 67 around the periphery of pocket 66, encapsulating exothermic composition 68 and forming the heat cell.

In some embodiments, such as described in U.S. Pat. No. 6,146,732 Davis, et al.; U.S. Pat. No. 6,074,413 Davis, et al.; U.S. Pat. No. 6,336,935, Davis et al: and U.S. Pat. No. 6,020,040, Cramer et al.; all incorporated herein by reference, the thermal pack has a unified structure comprising at least one continuous layer of a material. In FIG. 6, the base material 67 and the cover material 69 form continuous layers. The individual heat cells 62 are spaced apart and fixedly attached to or within the continuous layers. When heat cells fixed within or to the unified structure of the thermal pack are active, that is at a heat cell temperature of from about 35° C. to about 60° C., the narrow portion of the continuous layer(s) of material immediately surrounding each heat cell softens and acts as a hinge between the heat cells and between any remaining more rigid portion of the continuous layer or layers, bending preferentially more than either the heat cells or any cooler, more rigid portions. This provides good overall drape characteristics and conformity with body forms when heated, while maintaining structural support of the heat cells and/or preventing unacceptable stretching of structures of the continuous layer or layers during processing or use.

The continuous layer or layers typically comprises a material that is semi-rigid at a temperature of about 25° C. and is less rigid at a higher temperature. Different materials may be capable of satisfying these requirements provided that the thickness is adjusted accordingly. Such materials may include polyethylene, polypropylene, nylon, polyester, polyvinyl chloride, polyvinylidene chloride, polyurethane, polystyrene, saponified ethylene-vinyl acetate copolymer, ethylene-vinyl acetate copolymer, natural rubber, reclaimed rubber, synthetic rubber, and mixtures thereof. These materials may be used alone or coextruded with a low melt temperature polymer, such as ethylene vinyl acetate copolymer, low density polyethylene, and mixtures thereof. Such materials are capable of containing the exothermic composition and limiting oxygen flow into the pocket, and also provide sufficient rigidity to prevent the thermal pack from folding or bunching during use, preventing unacceptable stretching of structures of the continuous layer during processing or use, and deterring easy access to the heat cell contents.

The continuous layer or layers of material typically comprises polypropylene, and has a combined basis weight thickness of less than about 50 microns. Particularly suitable is a coextruded material having a first side of polypropylene and a second side of a low melt temperature copolymer, such as EVA, having a total material thickness of from about 20 microns to about 30 microns, available from Clopay Plastic Products, Cincinnati, Ohio, as P18-3161. When the polypropylene/EVA coextruded material is used, the polypropylene side is oriented to the outside (i.e., away from the exothermic composition).

Good overall drape characteristics and/or conformity with various body forms, and/or increased structural support to the thermal pack, may also be achieved by selectively placing the heat cells into positions fixed within or to the unified structure of the thermal pack which are sufficiently close to block some or all possible axes across the material of the continuous layer(s) which otherwise would pass uninterrupted between the heat cells, through the thermal pack, or select regions thereof, to minimize or eliminate undesirable, uninterrupted fold lines. As a result, the continuous layer or layers typically folds along a multiplicity of short interconnected fold lines oriented in a number of different directions relative to each other. Folding along a multiplicity of interconnected fold lines results in thermal packs that have good overall drape characteristics and readily conform to various body forms.

In one embodiment, the thermal pack has a unified structure comprising at least one continuous layer and a plurality of individual heat cells spaced apart and fixedly attached to or within said at least one continuous layer. These heat cells are spaced apart from each other and each cell functions independently of the rest of the cells. While the heat cells may comprise any suitable composition providing heat, such as exothermic compositions, microwaveable compositions, heat of crystallization compositions, and the like, the heat cell typically comprise a densely packed, particulate exothermic composition which substantially fills the available cell volume within the cell reducing any excess void volume and minimizing the ability of the particulate matter to shift within the cell. Alternatively, the exothermic composition may be compressed into a hard tablet or slug before being placed into each cell.

The exothermic composition typically comprises a mix of chemical compounds that undergo an oxidation reaction during use. The mix of compounds typically comprises iron powder, carbon, a metal salt(s), and water. Mixtures of this type react when exposed to oxygen, providing heat for several hours.

Suitable sources for iron powder include cast iron powder, reduced iron powder, electrolytic iron powder, scrap iron powder, pig iron, wrought iron, various steels, iron alloys, and the like, and treated varieties of these iron powders. There is no particular limitation to purity, kind, etc. so long as the iron powder can be used to produce heat-generation with electrically conducting water and air. Typically, the iron powder comprises from about 30% to about 80% by weight, e.g. from about 50% to about 70% by weight, of the particulate exothermic composition.

Active carbon is also useful in the particulate exothermic composition. There is no limitation to the kinds of active carbon used. The active carbon typically has superior water holding capabilities. Different carbons may be blended to reduce cost. Typically, the activated carbon, non-activated carbon, and mixtures thereof, comprise from about 3% to about 25%, more typically from about 8% to about 20%, e.g. from about 9% to about 15%, by weight, of the particulate exothermic composition.

Metal salts useful in the particulate exothermic composition include sulfates such as ferric sulfate, potassium sulfate, sodium sulfate, manganese sulfate, and magnesium sulfate; and chlorides such as cupric chloride, potassium chloride, sodium chloride, calcium chloride, manganese chloride, magnesium chloride and cuprous chloride. The metal salts often include sodium chloride, cupric chloride, and mixtures thereof. Typically, the metal salt(s) comprises from about 0.5% to about 10%, more typically from about 1.0% to about 5%, by weight, of the particulate exothermic composition.

The water used in the particulate exothermic composition may be from any appropriate source. There is no particular limitation to its purity, kind, etc. Typically, water comprises from about 1% to about 40%, more typically from about 10% to about 30%, by weight, of the particulate exothermic composition.

The exothermic composition typically is in the form of dry agglomerated granules, direct compaction articles, or mixtures thereof. Heat cells comprising compaction articles can be made by direct compaction of the dry ingredients into granules, pellets, tablets, slugs, or mixtures thereof. Any conventional tableting machine and compression pressures, up to the maximum provided by the machine, can be used. The direct compaction article typically ahs a density of greater than about 1 g/cm$^3$.

Activation of each cell may be accomplished by injecting water or salt solution, e.g., by needle, through the oxygen permeable layer into the hole or reservoir in the middle of the tablet or into the granular composition. Since the heat cell will begin to generate heat shortly after activation if exposed to oxygen in the air, the thermal pack is placed into an oxygen impermeable package, which may be evacuated of oxygen, and then sealed. Alternatively, water or salt solution can be added to the exothermic composition prior to the application of the second continuous layer, which forms the heat cell.

The tablets/slugs can have any geometric shape consistent with the shape of the heat cell, e.g., disk, triangle, square, cube, rectangle, cylinder, ellipsoid and the like, all or none of which may contain a hole through the middle or other reservoir. The heat cells typically have a disk or ellipsoid shape. The tablet/slug may have a concave configuration to the top and/or bottom of the tablet. The tablet/slug typically has a hole perpendicular to and through the middle of the top and bottom of the tablet. A water-carrying material having hydrous property and flexibility such as a super absorbent material, a spongy body, paper, synthetic resin-foam, rubber, cellulose, and the like may be placed in the hole or reservoir to gradually supply the water to the compressed particulate composition to prolong the exothermic reaction.

The size of the compacted article is limited only by the size of the punch and die available and/or used in the tableting machine, as well as the size of the heat cell pocket. A compacted disk typically has a diameter of from about 0.2 cm to about 10 cm. A compacted article having a geometric shape other than a disk may have a width at its widest point of from about 0.15 cm to about 20 cm and a length at its longest point of from about 1.5 cm to about 20 cm. The hole or reservoir should be large enough to substantially hold the prescribed amount of water and/or the water-carrying material. Typically, the hole has a diameter of from about 0.1 cm to about 1 cm. Each heat cell often has a similar volume of heat generating material and has similar oxygen permeability means. However, the volume of the heat generating material, shape of the heat cell, and oxygen permeability may be different from heat cell to heat cell as long as the resulting cell temperatures generated are within accepted therapeutic and safety ranges for their intended use.

The finished heat cell can have any geometric shape, e.g., disk, triangle, pyramid, cone, sphere, square, cube, rectangle, rectangular parallelepiped, cylinder, ellipsoid and the like. The heat cells typically have a disk shaped geometry having a cell diameter of from about 0.2 cm to about 10 cm and a height of from about 0.2 cm to about 1 cm. Oxygen permeability can be provided by selecting materials for the first and second continuous layers forming the pockets, and/or covering layer, that have the desired permeability properties. The permeability properties may be provided by microporous films or by films that have pores or holes formed therein. The formation of holes/pores may be via extrusion cast/vacuum formation or by hot or cold needle aperturing. The velocity, duration, and temperature of the thermogenic oxidation reaction of the particulate exothermic composition can be controlled by changing the area of contact with air and the oxygen diffusion/permeability.

In one embodiment, the thermal pack comprises at least one continuous layer of a material that exhibits the thermophysical characteristics specified herein. The continuous layer(s) of such material(s) is typically included as one or both of the layers used to form the heat cells. Alternatively, the heat cells may be mounted individually or in one or more groups to one or more continuous layers of a material that exhibits the thermophysical characteristics specified herein.

The finished disposable thermal pack is typically packaged in an air-impermeable package that prevents an oxidation reaction from occurring until desired, as described in U.S. Pat. No. 4,649,895, incorporated herein by reference. Alternatively, other means may also be used to prevent an oxidation reaction from occurring before desired, such as by placing air impermeable removable adhesive strips over the aeration holes in the heat cells. When the strips are removed, air is allowed to enter the heat cells and activate the oxidation reaction of the iron powder.

The thermal pack or other disposable article herein may further comprise an aromatic compound, a pharmaceutical active, a lotion, an emollient, a moisturizing agent, or mixtures thereof, to be delivered to the body, typically through the skin. For example, a pharmaceutical active such as disclosed in U.S. Pat. No. 6,488,959, incorporated herein by reference, may be added to an article comprising a thermal pack. Aromatic compounds include, but are not limited to, menthol, camphor, eucalyptus, benzaldehyde, citral, decanal, and aldehyde, and mixtures thereof. Pharmaceutical actives/therapeutic agents include, but are not limited to, antibiotics, vitamins, antiviral agents, analgesics, anti-inflammatory agents, antipruritics, antipyretics, anesthetic agents, antifungals, antimicrobials, and mixtures thereof.

Figure 7:
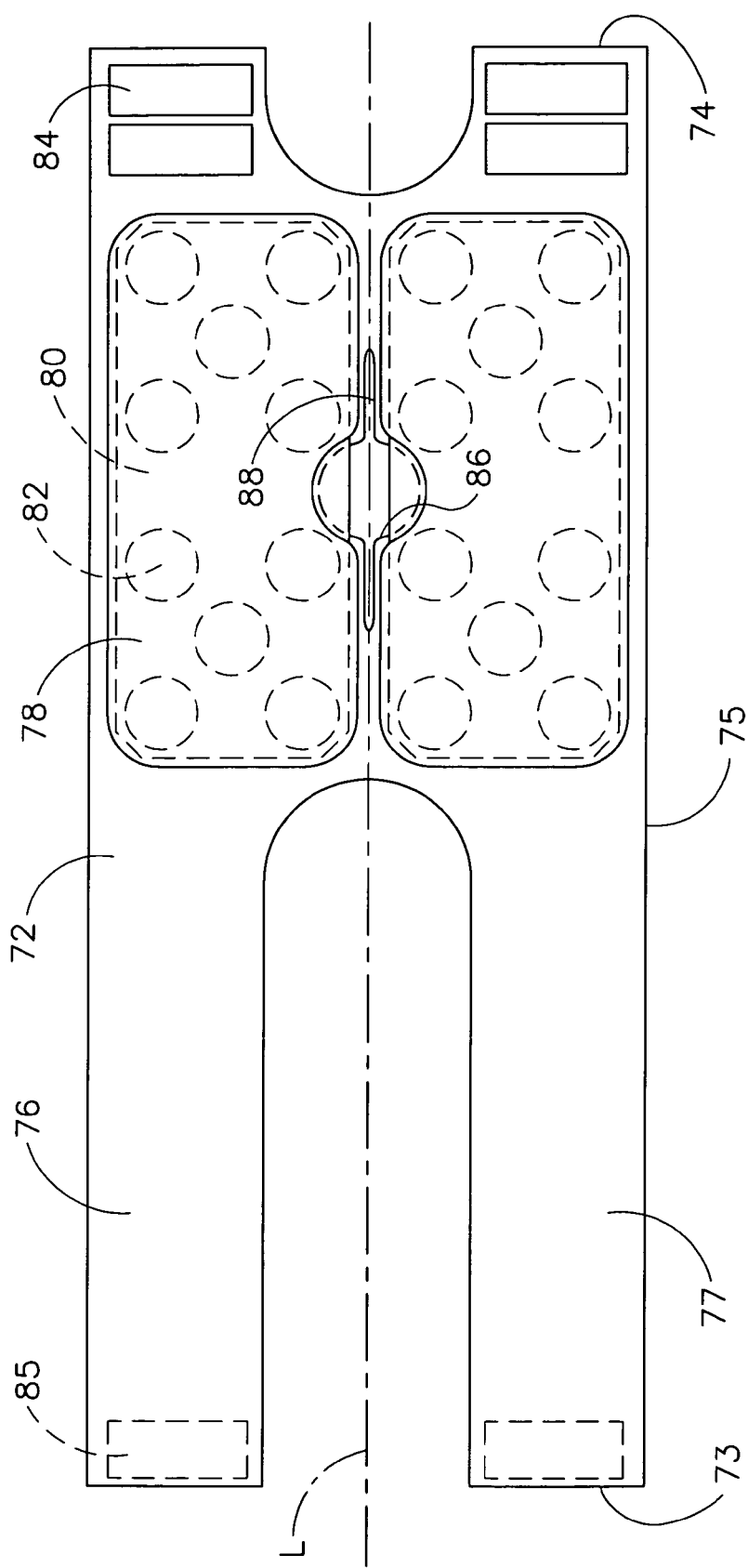
FIG. 7 is a plan view of another holder and system of the invention comprising a body conforming textile wrap holder and thermal packs capable of being removably held in close bodily contact by the holder.

FIG. 7 shows a plan view of another holder and system of the invention in the form of an elastic thermal uniaxial joint wrap and a thermal pack for use therewith. Examples of uniaxial-joint wrap holders are suitable size and shape, as well as thermal packs useful herein, are disclosed in U.S. Pat. Nos. 5,906,637 and 6,048,326, both incorporated herein by reference. In one embodiment, FIG. 7 illustrates a knee wrap in a full flat out position. In another embodiment, the product can be used as an elbow wrap. Holder 70 comprises a substantially rectangular piece of flexible material 72 having a longitudinal axis L. Flexible material 72 has a first end 73, a second end 74, a body portion 75 fixed between said first and second ends, a first strap portion 76 and a second strap portion 77. At least one of the body portion, first strap portion and second strap portion comprises one or more elastic structures and is capable of being stretched along longitudinal axis L. Flexible material 72 has a length when in a relaxed or stretched state, as measured in a direction parallel to longitudinal axis L from first end 73 to second end 74, which is great enough to encircle a user's knee or elbow.

The holder 70 further comprises a fastening system to hold it around a user's knee or elbow. The fastening system typically is reclosable. The fastening system typically is fixedly attached near or to a least one of the first and second ends of the holder. In one embodiment, each of a first strap portion 76 and a second strap portion 77 has at least one hook fastener portion 85 which can be independently fastened to loop fastener portion 84. Upon application of the holder to a knee, first end 73 of first strap portion 76 encircles behind the user's leg above the knee, and first end 73 of second strap portion 77 encircles behind the user's leg below the knee. The first ends of the first and second strap portions overlap the second ends 74 such that loop fastener portions 84 engage hook fastener portions 85. Other fastening systems, including adhesive fastening systems, can be used to securely affix the holder to the knee. Similarly, a holder may be affixed to a user's elbow. Typically, first strap portion 76 and second strap portion 77 comprise elastic regions and exhibit elastic behavior when stretched in a direction parallel to longitudinal axis L.

Flexible material 72 further comprises a body portion 75. For a knee holder, the width of body portion 75, measured in a direction transverse longitudinal axis L, typically is from about 15 cm to about 25 cm, more typically from about 18 cm to about 23 cm, e.g., from about 19 cm to about 21 cm. The width of upper strap portion 76 and lower strap portion 77, measured in a direction transverse longitudinal axis L, is less than the width of body portion 75, and typically is from about 2.5 cm to about 13 cm, more typically from about 4 cm to about 8 cm, e.g., from about 5 cm to about 7 cm.

Flexible material 72 further comprises an aperture 86 that aligns with the wearer's patella or olecranon to establish a convenient locating point for wrapping the wrap around the user's knee or elbow and to help properly position wrap 70 during use. At least one slit, such as slit 88, extends substantially longitudinally, e.g., from aperture 86, to enable flexible material 72 to stretch transverse to the longitudinal axis to accommodate bending of the user's knee or elbow. Slit 88 may be of any shape, but typically has a rectangular shape. For a knee holder, slit 88 typically is from about 15 cm to about 18 cm long.

In FIG. 7, at least one disposable thermal pack such as described above, e.g., thermal pack 80, is removably mounted to holder 70 by inserting it in a pocket 78 affixed to the holder. The pocket may be integrally formed in the holder, or it may be separately attached to the holder, e.g., by sewing, gluing or using mechanical fasteners. The pocket may have an opening or it may be made of mesh material to allow direct or substantial contact between the thermal pack and body. Alternatively, the pocket may be on the outside of the holder, and the pocket and/or the holder may have an opening therein so that the thermal pack is in direct or substantial contact with the body. When the thermal pack is expended, it can be removed from the holder and a new thermal pack placed within the pocket. The thermal pack may be secured within the pocket by the addition of a mechanical or adhesive fastening system, but typically is retained by the holder in the pocket simply by contractive forces and friction. Alternatively, the thermal pack may be affixed to the holder by employing a fastening system, such as a hook and loop mechanical fastening system or an adhesive fastening system. In one embodiment, a loop fastener portion is securely affixed to a surface of holder 70, e.g., by gluing it to the surface of the holder. A hook fastener portion is securely affixed to thermal pack 80, e.g., by gluing it to the thermal pack. When the thermal pack is expended, a new thermal pack comprising a hook fastener portion can be mounted to the holder in the desired position.

Figure 8:
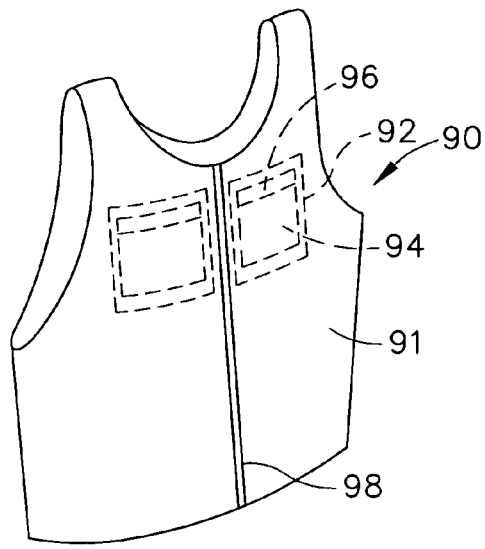
FIG. 8 is a perspective view of a holder and system of the invention comprising a body conforming shirt-like textile holder and articles capable of being removably held in close bodily contact by the holder.

FIG. 8 illustrates another holder and system of the invention comprising a body conforming shirt-like holder for removably holding at least one therapeutic article such as described above in close bodily contact. The holder is constructed to enclose a portion of the body in need of therapeutic treatment. The therapeutic article comprises a body facing side, a side opposite the body facing side, and a therapeutic agent. Typically, the side opposite the body facing side is liquid impervious. Both the therapeutic article and the holder typically are vapor permeable, and the article is disposable. Such an article is designed to provide the desired therapeutic benefit by delivering an effective amount of the therapeutic agent to the portion of the body in need of treatment when the article is held in close bodily contact by the holder. The therapeutic agent typically is transferable to the wearer's body, e.g., through the skin, in an effective amount to provide the therapeutic benefit. The therapeutic agent may comprise an aromatic compound, a pharmaceutical active, a lotion, an emollient, a moisturizing agent, a hearing agent, a cooling agent, or mixtures thereof.

In FIG. 8, the shirt-like holder 90 is constructed in the form of a vest (i.e., without arm extensions) comprising at least one elastic region 91. A therapeutic article such as a thermal pack as described above, e.g., thermal pack 94, can be removably mounted to holder 90 by employing one or more pockets, such as pocket 92. The pocket may be integrally formed in the holder, or it may be separately attached to the holder, e.g., by sewing, gluing or using mechanical fasteners. The pocket may have an opening or it may be made of mesh material to allow direct or substantial contact between the article and body. Alternatively, the pocket may be on the outside of the holder, and the pocket and/or the holder may have an opening therein so that the article may be in direct or substantial contact with the body. In another embodiment, the therapeutic article is removably mounted to holder 90 by employing a hook and loop fastening system. For example, the holder may comprise a first fastening material that cooperatively engages a second fastening material on the article and enables the article to be removably affixed to the holder. In one embodiment, a loop fastener portion is securely affixed to a surface of the holder, e.g., by gluing it to the surface. Alternatively, the loop fastener portion can be an integral part of the holder. For example, the holder or a portion thereof may be made of a material that can function as a loop fastener portion, such as a knit material. A hook fastener portion is securely affixed to the article, e.g., by gluing it to the article. The article is securely, but removably, affixed to the holder by engaging the hook fastening portion and the loop fastening portion. In another embodiment, the article can be removably affixed to the holder using an adhesive material, such as pressure sensitive adhesives or cohesive-adhesive fastening systems known in the art.

In the embodiments described above employing at least one pocket or where a loop fastener portion is affixed to the holder, the holder is constructed to hold the article in a selected location. In the alternative embodiment described above where the loop fastener portion is an integral part of the holder, the article with the affixed hook fastener portion may be affixed to any suitable portion of the holder comprising the loop material. When the article is expended, a new article comprising a hook fastener portion can be mounted to the holder in the selected location or a suitable position on the holder. As shown in FIG. 8, thermal pack 94 can be securely held in close bodily contact to provide heat to the body region to be treated (e.g., back, neck, shoulder, abdomen, etc.). Employment of this system involves placing the holder 90, with thermal pack 94 removably mounted in pocket 92, on the torso as customary depending on the precise shirt design.

Holder 90 further comprises fastening system 98, which can comprise hook and loop fasteners, buttons, a zipper, etc., to close the holder around the user's torso. In one embodiment, holder 90 is a wrap and fastening system 98 comprises at least two cooperating fastening materials e.g., hook and loop fastening materials, affixed to opposed surfaces of the holder that can be positioned to removably enclose a portion of the body in need of therapeutic, e.g., heat, treatment. Alternatively, the holder may be a tube, e.g., a pullover or T-shirt, which can be positioned to enclose a portion of the user's body, such as the torso, in need of treatment. In such designs, thermal pack 94 can be removably mounted in the chest and upper abdomen area using methods such as described above to provide improved thermal comfort by warming the center and core of the body. A fastening system 96, such as a hook and loop fastener or an adhesive fastener, can be employed to retain thermal pack 94 in pocket 92.

Figure 9:
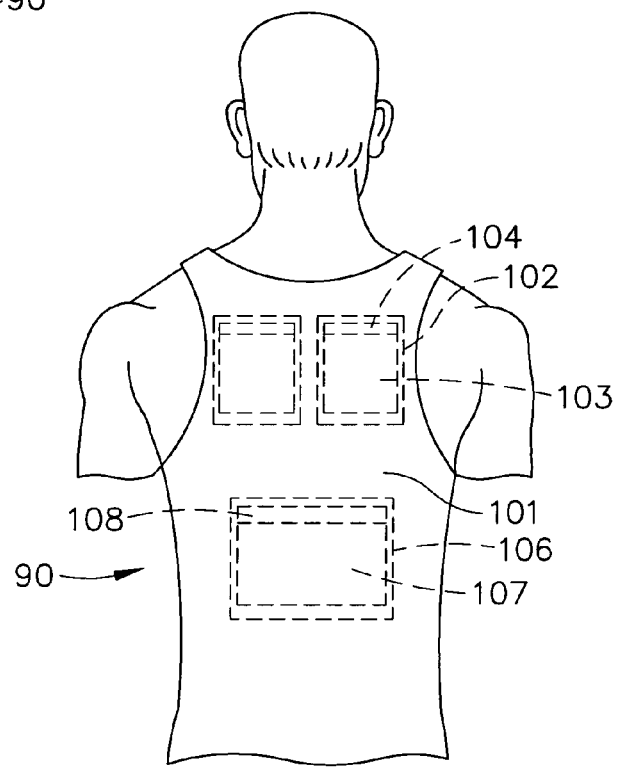
FIG. 9 is a rear view of the holder of FIG. 8 holding additional articles in close bodily contact.

FIG. 9 is a rear view of the holder 90 shown holding additional therapeutic articles, such as thermal packs 103 and 107 as described above, in close bodily contact. Holder 90 comprises elastic region 101 and pockets 102 and 106. As described above, the pockets may be integrally formed in the holder or they may be separately attached to the holder, e.g., by sewing, gluing or using mechanical fasteners. The pockets may have an opening or they may be made of mesh material to allow direct or substantial contact between the article and body. Alternatively, the pockets may be on the outside of the holder, and the pockets and/or the holder may have an opening therein so that the article may be in direct or substantial contact with the body. In this design, thermal packs 103 and 107 are removably held in close bodily contact by the holder by mounting them in pockets 102 and 106 to provide improved thermal comfort to the upper and lower back areas. Fastening systems 104 and 108, such as a hook and loop fastener or an adhesive fastener, can be employed to retain the thermal packs in the pockets. In other embodiments, hook and loop fasteners or adhesive materials can be used to removably affix the therapeutic articles to the holder.

Figure 10:
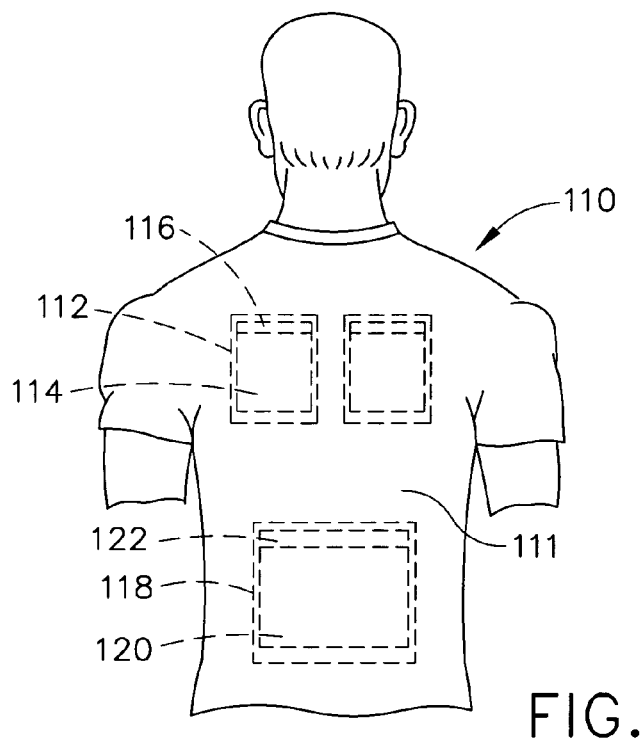
FIG. 10 is a rear view of another holder and system of the invention comprising a body conforming shirt-like textile holder and articles capable of being removably held in close bodily contact by the holder.

FIG. 10 is a rear view of another holder and system of the invention. In this embodiment, body conforming shirt-like holder 110 comprises arm extensions, which may be short sleeves as shown or longer sleeves. Holder 110 comprises elastic region 111 and pockets 112 and 118. As described above, the pockets may be integrally formed in the holder or they may be separately attached to the holder, e.g., by sewing, gluing or using mechanical fasteners. The pockets may have an opening or they may be made of mesh material to allow direct or substantial contact between the article and body. The pockets may be on the outside of the holder, and the pockets and/or the holder may have an opening therein so that the article may be in direct or substantial contact with the body. Thermal packs 114 and 120, such as described above, are removably held in close bodily contact by the holder by mounting them in pockets 112 and 118 to provide improved thermal comfort to the upper and lower back areas. Fastening systems 116 and 122, such as a hook and loop fastener or an adhesive fastener, can be employed to retain the thermal packs in the pockets. In other embodiments, hook and loop fasteners or adhesive materials can be used to removably affix the therapeutic articles to the holder.

Figure 11:
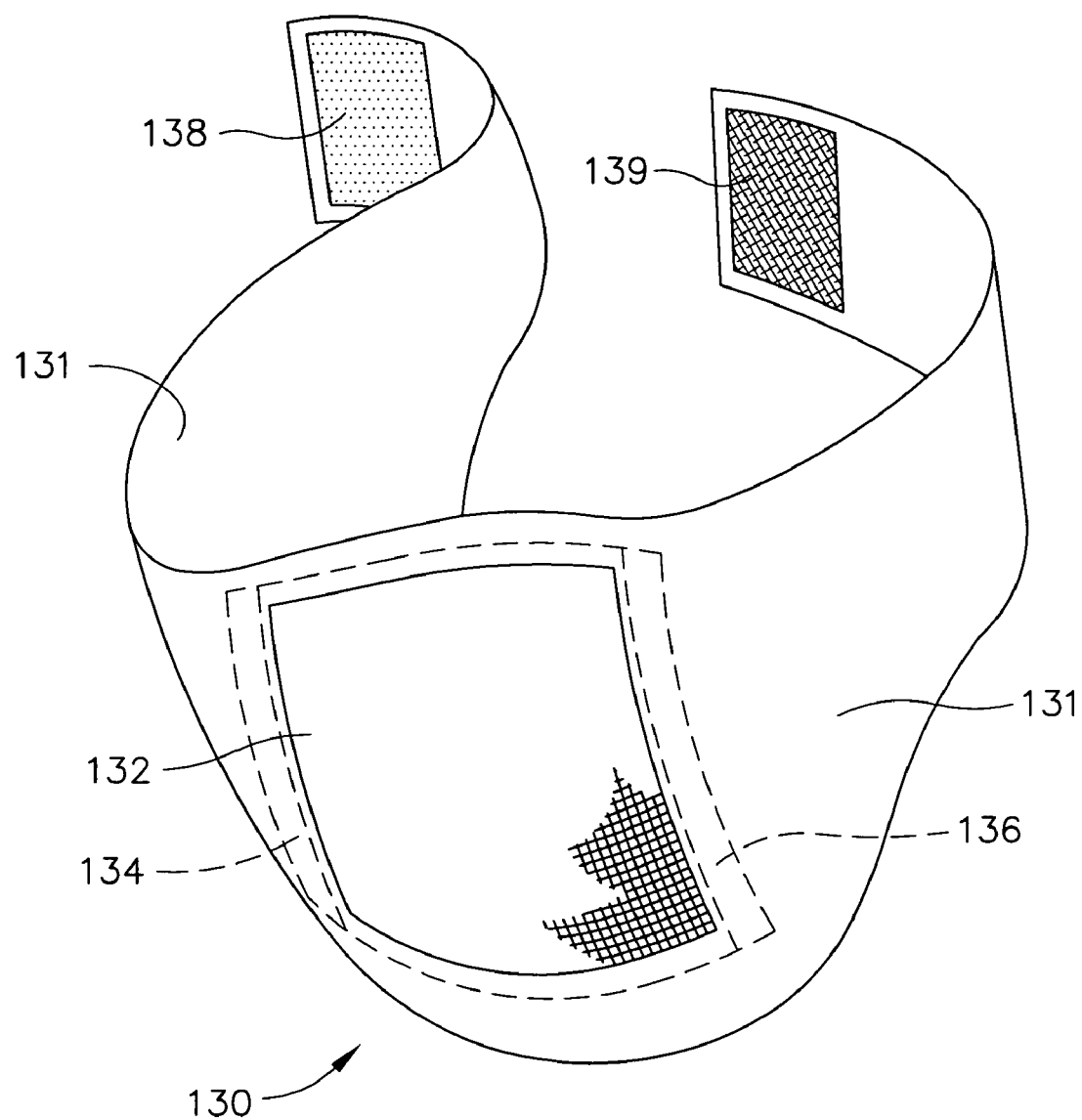
FIG. 11 is a perspective view of another holder and system of the invention comprising a body conforming textile wrap holder and a filter article capable of being removably held in close bodily contact over a user's mouth and nostrils.

FIG. 11 illustrates another holder and system of the invention. In this embodiment, holder 130 is a wrap constructed in the form of a face mask for removably holding at least one filter article, such as filter article 132, in close bodily contact over a user's mouth and nostrils. Holder 130 comprises at least one elastic region, such as elastic region 131. The article typically is disposable. The filter article may further comprise a therapeutic agent, such as a pharmaceutical active. Suitable filter articles herein are described in U.S. Pat. No. 6,928,657, incorporated herein by reference.

Filter article 132 can be removably mounted to holder 130 by employing fastening systems 134 and 136, which can be hook and loop fasteners or an adhesive fastener. In one example, the holder comprises a first fastening material and the filter article comprises a second fastening material that cooperatively engages the first fastening material and enables the filter article to be removably affixed to the holder. In one embodiment, the first and second fastening materials comprise mechanical fastening material, e.g., hook and loop fasteners. Alternatively, the filter article can be removably mounted to the holder by employing a pocket, such as described above.

Figure 12:
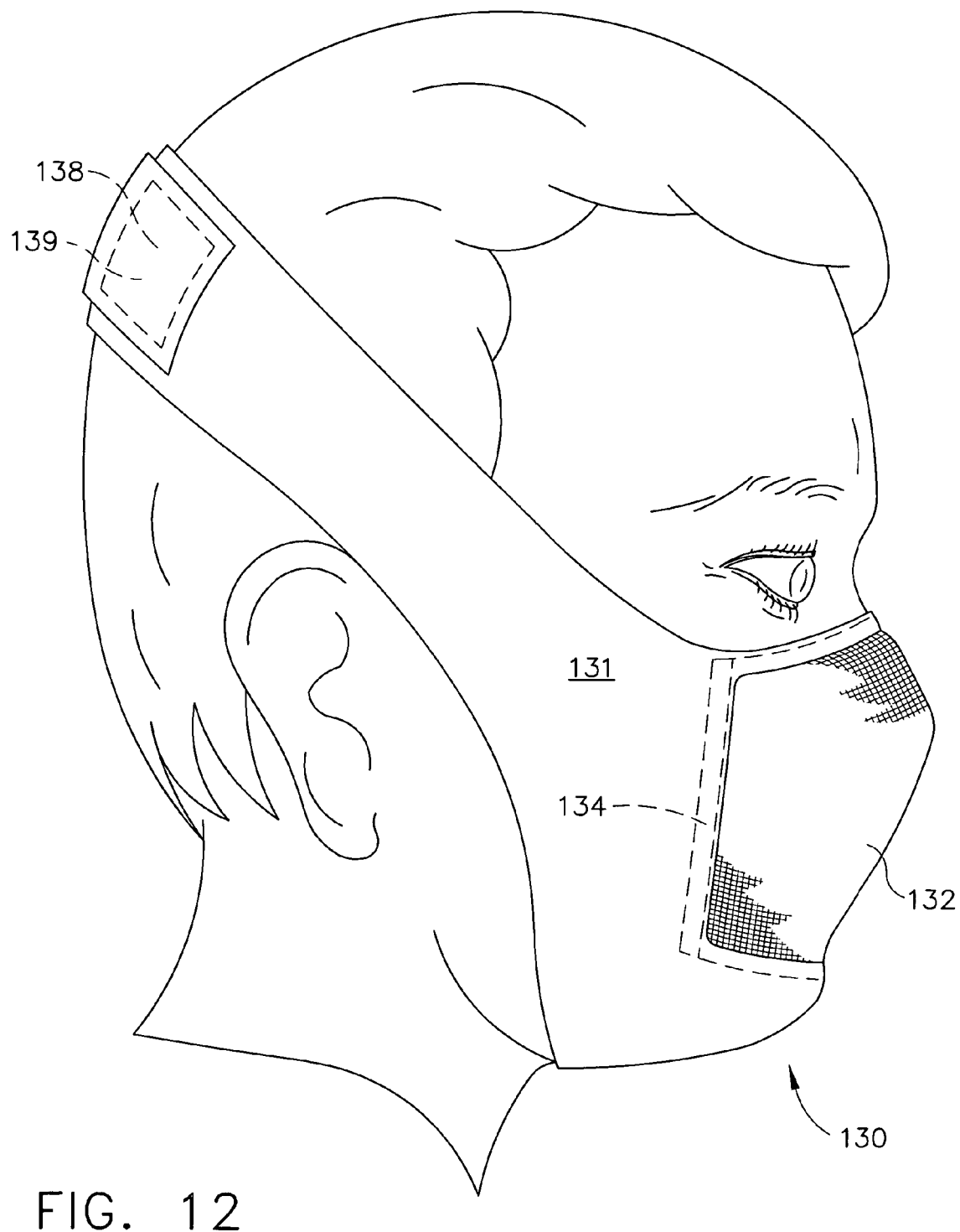
FIG. 12 is a side view of the holder and filter article of FIG. 11 being worn by a user.

Holder 130 comprises an additional fastening system to enable it to be affixed to the user's face. In one example, the holder comprises at least two cooperating fastening materials affixed to opposed surfaces of the holder that can be positioned to removably enclose at least a portion of the user's head. While various fastening systems can be used, FIG. 11 depicts the use of a conventional hook and loop fastening system comprising hook fastening portion 138 and loop fastening portion 139. FIG. 12 is a side view of the holder and filter article of FIG. 11 being worn by a user. The hook and loop fastening portions 138 and 139 are engaged so that the holder encloses a portion of the user's head. The holder is thus constructed to securely hold the filter article in close bodily contact over the mouth and nostrils, enabling at least partial filtering and removal of airborne contaminants, e.g., toxic and non-toxic contaminants, biological contaminants, other contaminants, and mixtures thereof. In another embodiment, the holder is a tube that can be positioned to enclose at least a portion of the user's head. Such a tube may have a shape similar to holder 130 when fastening portions 138 and 139 are engaged to close the holder.

Figure 13:
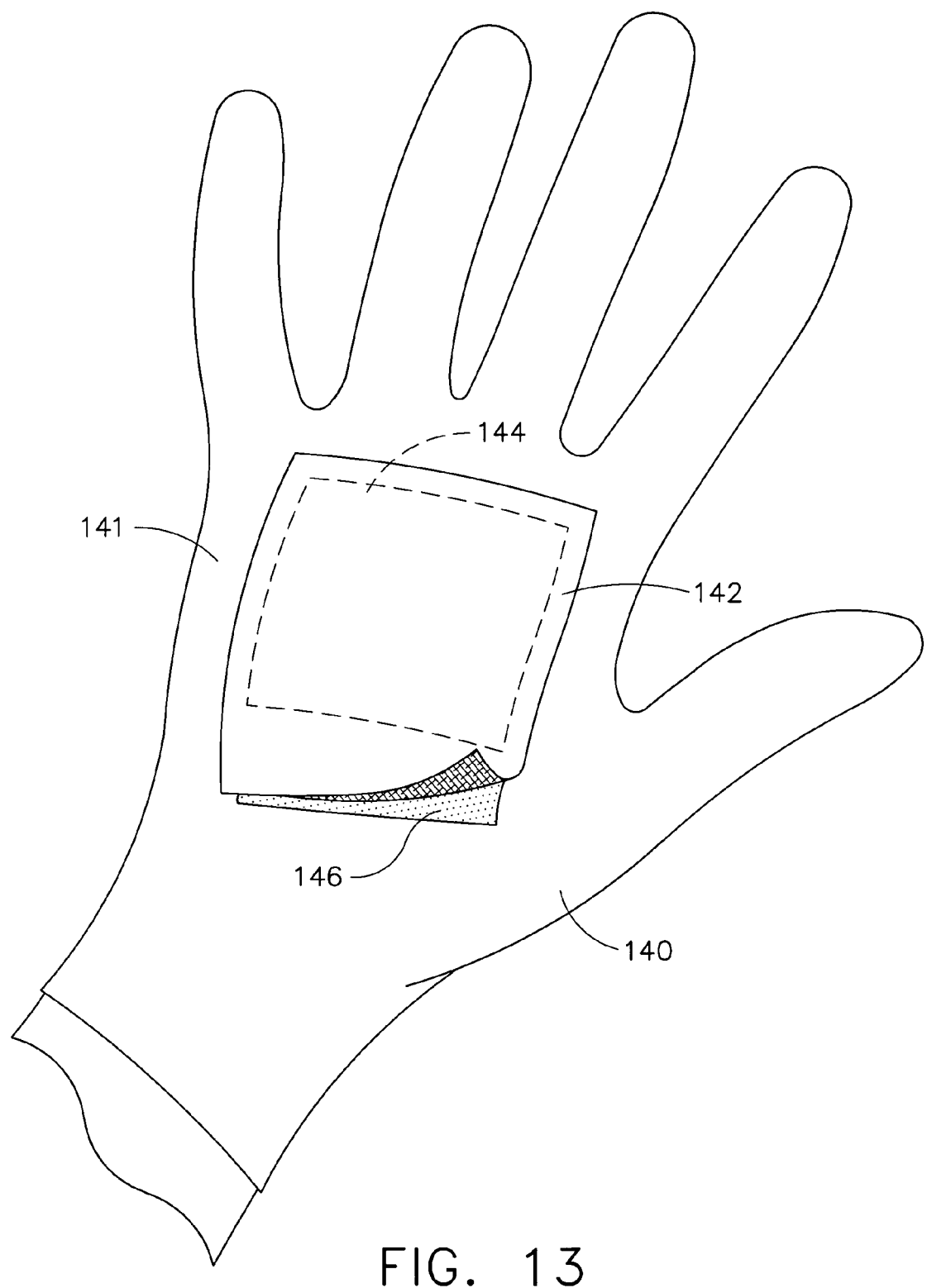
FIG. 13 is a perspective view of another holder and system of the invention comprising a body conforming textile glove-like holder and an article capable of being removably held in close bodily contact by the holder.

FIG. 13 is a perspective view of another holder and system of the invention comprising a body conforming textile glove-like holder and an article capable of being removably held in close bodily contact by the holder. The article may be a heating article, a therapeutic article, an absorbent article or a sensing article, as described above. In FIG. 13, holder 140 comprises at least one elastic region 141 and pocket 142 for holding the article, such as thermal pack 144. As described above, the pocket may be integrally formed in the holder or it may be separately attached to the holder, e.g., by sewing, gluing or using mechanical fasteners. The pocket may have an opening or it may be made of mesh material to allow direct or substantial contact between the article and the hand. In one embodiment, thermal pack 144 is removably held in close bodily contact by the holder by mounting it in pocket 142 to provide improved thermal comfort to the hand. Fastening system 146, such as a hook and loop fastener or an adhesive fastener, can be employed to retain the thermal pack in the pocket. Alternatively, the article can be removably mounted to the holder by employing fastening systems such as hook and loop fasteners or an adhesive fastener. For example, the holder can comprise a first fastening material and the article as second fastening material that cooperatively engages the first fastening material and enables the article to be removably affixed to the holder. In one embodiment, the first and second fastening materials comprise mechanical fastening material, e.g., hook and loop fasteners.

In another embodiment, the invention comprises a body conforming textile holder in the form of a sock or headgear, e.g., a hat or headband, and an article capable of being removably held in close bodily contact by the holder. The article may be a heating article, a therapeutic article, an absorbent article or a sensing article, as described above. The holder comprises at least one elastic region and may have at least one pocket for removably holding the article, e.g., a thermal pack, in close bodily contact such as described above. The pocket may be integrally formed in the holder or it may be separately attached to the holder, e.g., by sewing, gluing or using mechanical fasteners. The pocket may have an opening or it may be made of mesh material to allow direct or substantial contact between the article and the body. If the pocket is on the outside of the holder, the pocket and/or the holder may have an opening therein so that the article is in direct or substantial contact with the portion of the body being treated. A fastening system, such as a hook and loop fastener or an adhesive fastener, can be employed to retain the article in the pocket. Alternatively, the article can be removably mounted to the holder by employing fastening systems such as hook and loop fasteners or an adhesive fastener. For example, the holder can comprise a first fastening material and the article as second fastening material that cooperatively engages the first fastening material and enables the article to be removably affixed to the holder. In one embodiment, the first and second fastening materials comprise mechanical fastening material, e.g., hook and loop fasteners. A suitable holder in the form of a sock is disclosed in U.S. Pat. No. 5,230,333, incorporated herein by reference. A suitable holder in the form of headgear is disclosed in U.S. Pat. No. 5,395,400, incorporated herein by reference.

It will be appreciated that holders herein may have other configurations besides those shown and described. For example, the holder may comprise one or more additional straps, panels, or cut-out areas. Other holder styles, designs, and configurations that comprise at least an elastic region and an article attachment region of suitable properties are within the scope of the invention. As described above, the holder may comprise at least one extension or panel so long as it does not significantly interfere with the holding function of the holder.

The holders of the invention can be made by various methods known in the art. For a holder in the form of a tube, typically a blank for the holder is first knit in a tubular form using methods known to the art. For example, the elastic region, the article mounting region, and any article attachment region can by integrally knit. Appropriate knit patterns as described above can be used. Holder blanks can be formed by transversely cutting the tubular blank in a predetermined repeat pattern wherein a first transverse cut is made across the full width of the blank to form a top edge, and a second transverse cut is made across the full width of the tubular blank to form a bottom edge. The holder can be finished by forming turned welt elasticized bands about the periphery of the openings. A holder in the form of a wrap can be constructed by knitting a flat blank for the holder and then cutting and sewing the blank using various methods known to the art. Alternatively, a wrap holder can be made by forming a tubular blank as described above and then slitting the blank along one end. The ends and edges can then be finished, e.g., by sewing. A fastening system such as a reclosable hook and loop fastening system can be affixed along the ends of the holder, as described above.

The invention also relates to a method for treating acute, recurrent, and/or chronic pain, including muscular, skeletal, and/or referred pain, by topically applying heat to the afflicted body part of a person suffering such pain, using the heat delivery system comprising a holder and thermal pack herein. The method comprises maintaining a skin temperature to the afflicted area of from about 32° C. to about 50° C. by applying the thermal pack(s) to the afflicted area, for from about twenty seconds to about twenty-four hours, typically from about twenty minutes to about twenty hours, e.g. from about eight hours to about twelve hours. The length of time of maintaining the skin temperature within the above range may be selected by the person needing such treatment. The desired therapeutic benefits can thus be achieved without adverse events, such as skin burns that may be incurred by using a high temperature for a long period of time. Typically, the method comprises maintaining a sustained skin temperature of from about 32° C. to about 43° C., for a time period of greater than about 1 hour, typically greater than about 4 hours, e.g. about 24 hours, to substantially relieve acute, recurrent, and/or chronic pain, including skeletal, muscular, and/or referred pain. The method may substantially prolong relief, for example, for at least about 2 hours, typically for at least about 8 hours, more typically for at least about three days, from such pain, even after the heat source is removed from the afflicted body part.

Test Method for Measuring the Holding Force (HF) of Materials Using A "Constant-Rate-of-Extension (CRE) Ball Force Test"

Overview: This method measures a force (HF) that is related to the holding force exerted by an extensible material when holding an article against a wearer's body.

Terminology: The Holding Force (HF) is the force exerted by a material when distending it with a force applied at right angles to the plane of the material, under the specified conditions. The angle of application of force and the area of the material upon which the force is applied varies continuously as the material stretches when tested as directed in this method. In the Constant-Rate-of-Extension (CRE) tensile testing machine, the rate of increase of the specimen length is uniform with time.

Summary of Test Method: Set up the tensile testing machine for performing this test in accordance with both the manufacture's instructions and procedures presented herein. A specimen of material is securely clamped without tension within a "Ball Burst Test" attachment. A force is exerted against the specimen by a polished, hardened steel ball attached to the tensile testing machine. Holding Force (HF) data are recorded as a function of extension distance.

Apparatus: Tensile testing machine, of the constant-rate-of-extension (CRE) type. Equipment includes an Imada DPZ High Performance Programmable Digital Force Gauge: Model DPZ-4, and an Imada Motorized Vertical Test Stand: Model MX-110-S Test Stand w/Digital Distance Meter, both available from Imada, Incorporated, Northbrook, Ill. The Force Ball Attachment (modified "Ball Burst Test" attachment) consists of a clamping mechanism to hold the specimen and a steel ball attached to the moveable force gauge of the tensile testing machine. The circular opening and ring clamp has an internal diameter of 5.1 cm (2.0 in). The polished steel ball connected to the force gauge has a diameter of 1.6 cm (0.62 in).

Sampling and Specimen Preparation: The specimen is taken from the elastic region of the holder. Clamp the specimen in the ring clamp of the apparatus. The specimen must be of sufficient diameter to be held securely within the 5.1 cm (2.0 in) diameter ring clamp. The specimen may not require cutting if there is ample room to securely clamp the specimen in the apparatus. Ensure the specimen is free of folds, creases, or wrinkles, and is without tension when clamped. If the specimen is not uniform (e.g., it has a pattern, stitching, or a seam, etc.), ensure that the area tested is representative of the elastic region.

Procedure:

Place the specimen in the ring clamp, without tension, and fasten securely.

Move the Force Ball to a position immediately adjacent the specimen. Make sure there is no force applied to the ball by the specimen (HF-0.0=0 kgf).

Set the distance meter to zero (0 cm elongation).

Start the CRE machine and maintain a speed of 25.4+/−10 cm/min (10.0+/−0.5 in/min). Continue that speed until the specimen is extended at least 6.5 cm (2.6 in) or until a force of 2.0 kgf (4.5 lbf) is reached.

While the CRE machine and Force Ball are elongating the specimen, record Holding Force and elongation data at 0.5 second intervals.

Create a standard stress/strain curve (Holding Force versus elongation distance) with the resulting data.

Determine Holding Force (HF) at the appropriate elongation distances.

In the above method:

HF-0.0 is the force at 0 cm specimen elongation, i.e., the start of data collection. HF-0.0 should be 0 kgf at 0 cm elongation.

HF-1.0 is the force (kgf) at 1.0 cm Force Ball extension distance.

HF-2.0 is the force (kgf) at 2.0 cm Force Ball extension distance.

HF-2.5 is the force (kgf) at 2.5 cm Force Ball extension distance.

HF-3.0 is the force (kgf) at 3.0 cm Force Ball extension distance.

HF-4.0 is the force (kgf) at 4.0 cm Force Ball extension distance.

HF-5.0 is the force (kgf) at 5.0 cm Force Ball extension distance.

HF-5.5 is the force (kgf) at 5.5 cm Force Ball extension distance.

All limits and ranges specified herein include all narrower ranges, limits, and amounts that are within the specified limits and ranges, and such narrower ranges and limits may be claimed even though those limits and ranges are not separately listed.

While particular embodiments of the present invention have been illustrated and described, various other changes and modifications can be made without departing from the spirit and scope of the invention. It is therefore intended to cover all such changes and modifications that are within the scope of this invention.

What is claimed is:

1. An absorbent system comprising:
   a) a body conforming, reusable, washable, textile holder for removably holding at least one absorbent article in close bodily contact, said holder being a wrap or tube constructed to enclose a portion of the body where the absorbent article is to be held, and comprising an elastic region comprising elastic woven or knit material suitable for use in a reusable, washable holder, said elastic woven or knit material suitable for use in a reusable, washable holder, said elastic region having a high stretch in both the lateral and longitudinal directions as measured by having a Holding Force (HF-4.0) of greater than about 0.1 kgf and a Holding Force (HF-2.5) of less than about 1.0 kgf; and
   b) at least one absorbent article capable of being removably held in close bodily contact by said holder, said article comprising a liquid pervious body facing side, a liquid impervious side opposite the body facing side, and an absorbent component between the liquid pervious side and the liquid impervious side, wherein the liquid pervious side and the liquid impervious side are arranged to form a unitary structure.

2. A system according to claim 1 wherein both the absorbent article and the holder are vapor permeable.

3. A system according to claim 1 wherein the absorbent article is disposable.

4. A system according to claim 1 wherein the holder comprises knit material and elastomeric fiber material.

5. A system according to claim 1 wherein the elastic region of the holder has a Holding Force (HF-3.0) of less than about 1.0 kgf.

6. A system according to claim 1 wherein the elastic region of the holder has a Holding Force (HF-5.0) of less than about 1.0 kgf.

7. A system according to claim 1 wherein the holder is constructed to hold the absorbent article in a selected location.

8. A system according to claim 7 wherein the holder comprises at least one pocket for receiving and supporting the absorbent article.

9. A system according to claim 1 wherein the holder comprises a first fastening material and the absorbent article comprises a second fastening material that cooperatively engages the first fastening material and enables the absorbent article to be removably affixed to the holder.

10. A system according to claim 9 wherein the first and second fastening materials comprise mechanical fastening material.

11. A system according to claim 1 wherein the absorbent article is removably affixed to the holder using adhesive material.

12. A system according to claim 1 wherein the holder comprises at least two cooperating fastening materials affixed to opposed surfaces of the holder that can be positioned to removably enclose the portion of the body where the absorbent article is to be held.

13. A system according to claim 12 wherein the fastening materials comprise mechanical fastening material.

14. A system according to claim 1 wherein the absorbent article comprises a therapeutic agent that is transferable to the wearer's body in an effective amount to provide a desired therapeutic benefit.

15. A system according to claim 14 wherein the therapeutic agent comprises an aromatic compound, a pharmaceutical active, a lotion, an emollient, a moisturizing agent, or mixtures thereof.

16. A system according to claim 1 wherein the absorbent article is designed for wound care.

17. An absorbent system comprising:
   a) a body conforming, reusable, washable, textile holder for removably holding at least one absorbent article in close bodily contact, wherein the holder is a wrap comprising at least two cooperating fastening materials affixed to opposed surfaces of the holder that can be positioned to removably enclose as portion of the body where the absorbent article is to be held, and comprising an elastic region comprising elastic woven or knit material suitable for use in a reusable, washable holder, said elastic region having a high stretch in both the lateral and longitudinal directions as measured by having a Holding Force (HF-4.0) of greater than about 0.1 kgf and a Holding Force (HF-2.5) of less than about 1.0 kgf; and
   b) at least one absorbent article capable of being removably held in close bodily contact by said holder, said article comprising a liquid pervious body facing side, as liquid impervious side opposite the body facing side, and an absorbent component between the liquid pervious side and the liquid impervious side, wherein the liquid pervious side and the liquid impervious side are arranged to form a unitary structure.

18. A system according to claim 17 wherein the fastening materials comprise mechanical fastening material.

19. A system according to claim 17 wherein the elastic region of the holder has a Holding Force (HF-3.0) of less than about 1.0 kgf.

20. An absorbent system comprising:
a) a body conforming, reusable, washable, textile holder for removably holding at least one absorbent article in close bodily contact, wherein the holder is a tube that can be positioned to enclose a portion of the body where the absorbent article is to be held, and comprising an elastic region comprising elastic woven or knit material suitable for use in a reusable, washable holder, said elastic region having a high stretch in both the lateral and longitudinal directions as measured by having a Holding Force (HF-4.0) of greater than about 0.1 kgf and a Holding Force (HF-2.5) of less than about 1.0 kgf; and
b) at least one absorbent article capable of being removably held in close bodily contact by said holder, said article comprising a liquid pervious body facing side, a liquid impervious side opposite the body facing side, and an absorbent component between the liquid pervious side and the liquid impervious side, wherein the liquid pervious side and the liquid impervious side are arranged to form a unitary structure.

21. A system according to claim 20 wherein the elastic region of the holder has a Holding Force (HF-3.0) of less than about 1.0 kgf.

22. A system according to claim 20 wherein the holder is a glove, headgear, or a sock.

* * * * *

UNITED STATES PATENT AND TRADEMARK OFFICE
CERTIFICATE OF CORRECTION

PATENT NO. : 7,846,145 B2  
APPLICATION NO. : 11/269255  
DATED : December 7, 2010  
INVENTOR(S) : Jerry E. Carstens Page 1 of 1

It is certified that error appears in the above-identified patent and that said Letters Patent is hereby corrected as shown below:

Column 7, line 2, delete "yams" and insert --yarns--

Claim 1, lines 46-48, delete "said elastic woven or knit material suitable for use in a reusable washable holder,"

Claim 17, line 47, delete "as" and insert --a--

Signed and Sealed this  
First Day of February, 2011

David J. Kappos  
*Director of the United States Patent and Trademark Office*

UNITED STATES PATENT AND TRADEMARK OFFICE
CERTIFICATE OF CORRECTION

| | | |
|---|---|---|
| PATENT NO. | : 7,846,145 B2 | Page 1 of 1 |
| APPLICATION NO. | : 11/269255 | |
| DATED | : December 7, 2010 | |
| INVENTOR(S) | : Jerry E. Carstens | |

It is certified that error appears in the above-identified patent and that said Letters Patent is hereby corrected as shown below:

Column 7, line 2, delete "yams" and insert --yarns--

Claim 1, Column 23, lines 46-48, delete "said elastic woven or knit material suitable for use in a reusable washable holder,"

Claim 17, Column 24, line 47, delete "as" and insert --a--

This certificate supersedes the Certificate of Correction issued February 1, 2011.

Signed and Sealed this
First Day of March, 2011

David J. Kappos
*Director of the United States Patent and Trademark Office*